(12) United States Patent
Fujita et al.

(10) Patent No.: US 6,261,737 B1
(45) Date of Patent: Jul. 17, 2001

(54) POLYMETHINE COMPOUNDS, METHOD OF PRODUCING SAME, AND USE THEREOF

(75) Inventors: Shigeo Fujita, Osaka; Nobuaki Sasaki, Kyoto; Yasuhisa Iwasaki, Nara, all of (JP)

(73) Assignee: Yamamoto Chemicals, Inc., Osaka (JP)

( * ) Notice: Subject to any disclaimer, the term of this patent is extended or adjusted under 35 U.S.C. 154(b) by 0 days.

(21) Appl. No.: 09/447,257

(22) Filed: Nov. 23, 1999

(30) Foreign Application Priority Data

Nov. 30, 1998 (JP) .................................................. 10-356927

(51) Int. Cl.$^7$ .............................. G03C 1/72; G03F 7/004
(52) U.S. Cl. ...................... 430/270.1; 430/302; 430/944; 430/945; 101/453; 101/467; 8/659; 8/690
(58) Field of Search .................................. 430/270.1, 302, 430/944, 945; 101/453, 467; 8/659, 690

(56) References Cited

U.S. PATENT DOCUMENTS 4,871,656 * 10/1989 Parton et al. ..................... 430/522

FOREIGN PATENT DOCUMENTS

| 0387357-A1 | * | 9/1990 | (EP) | ............................. | C07D/209/70 |
| 0438123-A2 | * | 7/1991 | (EP) | ................................. | C08F/2/46 |
| 1006116-A1 | * | 6/2000 | (EP) | ........................... | C07D/491/056 |

* cited by examiner

Primary Examiner—Hoa Van Le
Assistant Examiner—Barbara Gilmore
(74) Attorney, Agent, or Firm—Birch, Stewart, Kolasch & Birch, LLP

(57) ABSTRACT

The invention provides near infrared absorbers showing high light-to-heat conversion efficiency and high sensitivity to laser beams whose emission region is within the range of 750 nm to 900 nm, plates for direct printing plate making, and novel compounds which can be used in such absorbers or plates. The compounds are polymethine compounds of the general formula (I) shown below and the near infrared absorbers comprise the polymethine compounds.

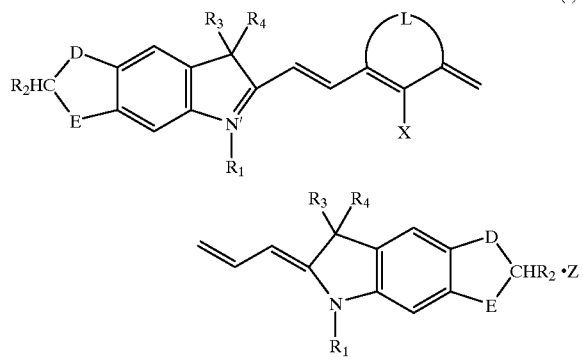

In the formula, $R_1$ represents an alkyl group, which may optionally be substituted, $R_2$ represents a hydrogen atom or a lower alkyl group, $R_3$ and $R_4$ each independently represents a lower alkyl group or $R_3$ and $R_4$ may combinedly form a cyclic structure, L is an alkylene group which is required for the formation of a cyclic structure and may optionally be substituted, one or more carbon atoms of which cyclic structure may be replaced by some other atom(s) or atomic group(s), D and E each independently represents an oxygen atom or a methylene group, X represents a hydrogen or halogen atom or a substituted amino group, and Z represents a charge-neutralizing ion.

10 Claims, 7 Drawing Sheets

POLYMETHINE COMPOUNDS, METHOD OF PRODUCING SAME, AND USE THEREOF

INDUSTRIAL FIELD OF APPLICATION

The present invention relates to a novel polymethine compound, a method of producing the same and a near infrared absorber comprising the same. The polymethine compound of the present invention has an absorption region in the near infrared region of 750–900 nm and can be utilized as a near infrared absorber for use in image recording utilizing laser beams, for instance, as a near infrared absorber in plate making utilizing laser beams or in producing laser heat-sensitive recording media. It can further be utilized as a spectral sensitization dye in electrophotography or silver halide photography, or a dye for optical disks, for instance.

PRIOR ART

In recent years, with the progression of laser technology, image recording systems utilizing laser beams have been explored in high-speed recording or high-density, high-image-quality recording. Thus, for example, image forming systems using laser heat-sensitive recording materials or laser thermal transfer recording materials have been studied in recording systems where a laser beam is converted to heat. Furthermore, the spread of computers, the rapid progress in electronics, and improvements in digital image processing technology have formed the backdrop for attempts to develop the so-called computer-to-plate technique (CTP plate making technique), which makes printing plates directly from digital data possible.

In the system of recording images through conversion of laser beams to heat (laser thermal recording system), a light absorber appropriate to the laser wavelength is used, and the light absorbed is converted to heat to form images. However, unless the laser output is increased to a considerable extent, the heat energy required for image formation cannot hardly be obtained. Therefore, the advent of a light absorber with good light-to-heat conversion efficiency is desired. In laser thermal recording materials, semiconductor lasers are generally used which have a light emitting region in the near infrared region of 750 nm to 900 nm. Near infrared absorbers appropriate to such laser wavelengths generally absorb light in the visible region as well and tend to disadvantageously cause coloration of the plain ground. Thus, a near infrared absorber that absorbs less light in the visible region is desired.

In the CTP plate making technology, known plate making methods are classifiable into the one comprising irradiating with a laser beam, the one comprising writing by means of a thermal head, the one comprising partially applying a voltage by means of a pin electrode, the one comprising forming an ink-repelling or ink-receiving layer with an ink jet, and so forth. Among them, the method which uses a laser beam is superior in resolution and in rate of plate making to other techniques, so that various image forming techniques have been investigated for said method.

Further, recently, small-sized, high-output inexpensive semiconductor lasers having a light emitting region in the near infrared region (750 nm to 900 nm) have become readily available and are becoming useful as exposure light sources in plate making.

There are two types of direct plate making utilizing laser beams, namely the photosensitive type and heat-sensitive type. As the photosensitive type plate material, there are known the electrophotographic system using an organic semiconductor (OPC), the silver salt system using a silver salt, and so on. These plate materials require a large-size and expensive apparatus for the manufacture thereof and are relatively expensive as compared with the conventional PS plates. There is also the problem of waste developer treatment.

Heat-sensitive plate materials are disadvantageous in that they are low in sensitivity as compared with the photosensitive type plate materials. Nevertheless, they have been intensively investigated since they can be handled in ordinary rooms (lighted rooms) and the corresponding apparatus are small in size and are inexpensive.

The heat-sensitive plate materials all require a light-to-heat conversion layer for converting light to heat. This light-to-heat conversion layer contains a light-to-heat conversion agent, for example a near infrared absorber. It is essential for this light-to-heat conversion agent to absorb the laser beam used and, for attaining improved sensitivity, it is necessary that the ability thereof to absorb the laser beam used and the light-to-heat conversion efficiency be higher.

The light-to-heat conversion agent includes pigment type and dye type substances. Carbon black is generally used as a pigment type substance. While various substances have been proposed as dye type ones, polymethine compounds are in general use. With carbon black, there is a wide selection of lasers to choose from. However, car bon black is generally less capable of absorbing laser beams as compared with dy e type substances, so that it is necessary to increase the amount thereof. A high-level dispersion technique is also required.

In cases where a dye type substance is used, it is necessary that it be highly capable of absorbing the laser beam used and that it be compatible with other components such as the image forming component and resin binder or soluble in the solvent employed.

Polymethine compounds have a methine chain linked by conjugated double bonds within the molecule and have absorption bands within the broad region from the visible to the near infrared region (340 to 1,400 nm) and have a high extinction coefficient at the absorption maximum. For these and other reasons, they are used in various fields, for example as photosensitive dyes for silver salt photography, photosensitive dyes for electrophotography, dyes for laser recording, or dyes for laser beam generation.

Although the polymethine compounds are high ly capable of absorbing laser beams, they are problems: matching with the laser beam to be used is necessary and known compounds are generally poor in light stability and poorly compatible with image forming substances and binder resins, among others.

A number of such polymethine compounds are already known. For instance, the compound A shown below is described in JP Kokai S63-319191 (page 3, Compound 9 as a specific example), and the compound B shown below is described in JP Kokai H02-229865 (page 6, Production Example 3).

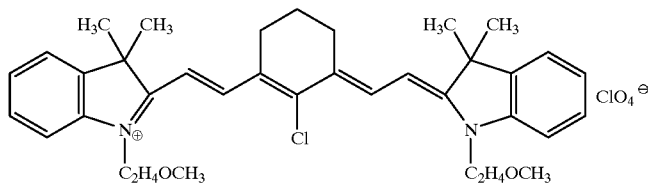

Compound A

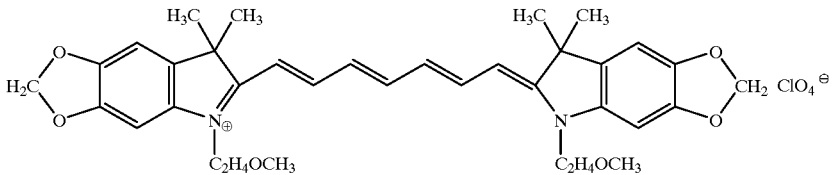

Compound B

However, the compounds A and B both have a maximum absorption wavelength within the range of 785 to 795 nm and are insufficiently sensitive to small-size, high-output lasers having a light emission region at 820 to 870 nm, which are currently under investigation as most likely candidates for use. As compared with the compound B, the compound A has improved light stability as a result of the introduction of a ring structure into the methine chain but it has drawbacks, such as poor solubility in solvents and poor compatibility with resins and therefore the range of choice of binder resin is restricted.

Accordingly, the primary object of the present invention is to provide a polymethine compound which is less absorptive in the visible region of light and is highly sensitive to beams from semiconductor lasers having light emission regions in the near infrared region (750 nm–900 nm) and is suited for use as a near infrared absorber or for use in the light-to-heat conversion layers of laser thermal recording media or original plates for direct plating for printing.

SUMMARY OF THE INVENTION

As a result of investigations made in an attempt to solve the problems such as mentioned above, the present inventors found that the novel polymethine compounds specified below are less absorptive in the visible region, highly sensitive to beams from semiconductor lasers having light emission regions in the near infrared region (750 nm–900 nm) and highly efficient in light-to-heat conversion and can be used as near infrared absorbers readily processible for various applications. Based on these findings, the present invention has now been completed.

In a first aspect, the present invention provides a polymethine compound represented by the genera l formula (I):

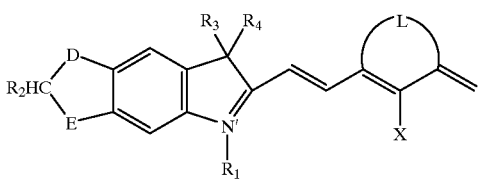

(I)

-continued

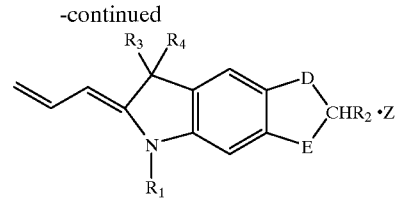

wherein $R_1$ represents an alkyl group, which may optionally be substituted, $R_2$ represents a hydrogen atom or a lower alkyl group, RD and $R_4$ each independently represents a lower alkyl group or $R_3$ and $R_4$ may combinedly form a cyclic structure, L is an alkylene group which is required for the formation of a cyclic structure and may optionally be substituted, one or more carbon atoms of which cyclic structure may be replaced by some other atom(s) or atomic group(s), D and E each independently represents an oxygen atom or a methylene group, X represents a hydrogen or halogen atom or a substituted amino group, and Z represents a charge-neutralizing ion.

In a second aspect, the present invention provides a method of producing the above polymethine compound of general formula (I) which comprises subjecting an indolenium compound represented by the general formula (II):

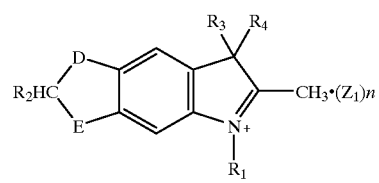

(II)

wherein $R_1$ represents an alkyl group, which may optionally be substituted, $R_2$ represents a hydrogen atom or a lower alkyl group, $R_3$ and $R_4$ each independently represents a lower alkyl group or $R_3$ and $R_4$ may combinedly form a cyclic structure, D and E each independently represents an oxygen atom or a methine group, $Z_1$ represents a charge-neutralizing ion and n represents an integer of 0 or 1, and a diformyl compound represented by the general formula (III):

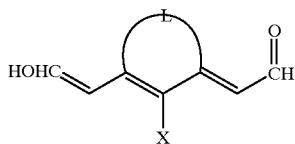

(III)

wherein X represents a hydrogen or halogen atom or a substituted amino group and L is an alkylene group which is required for the formation of a cyclic structure and may optionally be substituted, one or more carbon atoms of which cyclic structure may be replaced by some other atom(s) or atomic group(s), or a dianil compound represented by the general formula (IV):

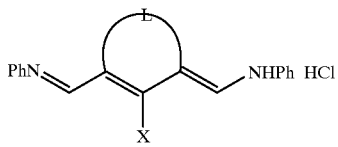

(IV)

wherein X re presents a hydrogen or halogen atom or a substituted amino group and L is an alkylene group which is required for the formation of a cyclic structure and may optionally be substituted, one or more carbon atoms of which cyclic structure may be replaced by some other atom(s) or atomic group(s), to condensation reaction in the presence of a fatty acid salt and a dehydrating organic acid.

In a third aspect, the present invention provides a near infrared absorber which comprises the polymethine compound according to the above-mentioned first aspect of the invention.

In a fourth aspect, the present invention provides an original plate for direct plating for printing comprising a light-to-heat conversion layer formed on a substrate, characterized in that said light-to-heat conversion layer contains the polymethine compound according to the above-mentioned first aspect of the invention.

In a fifth aspect, the present invention provides a method of making a printing plate which comprises irradiating the original plate for direct plating according to the above-mentioned fourth aspect of the invention with a laser beam from a light source laser which has a light emission wavelength region within the range of 750 nm to 900 nm.

DESCRIPTION OF THE PREFERRED EMBODIMENTS

Figure 1:
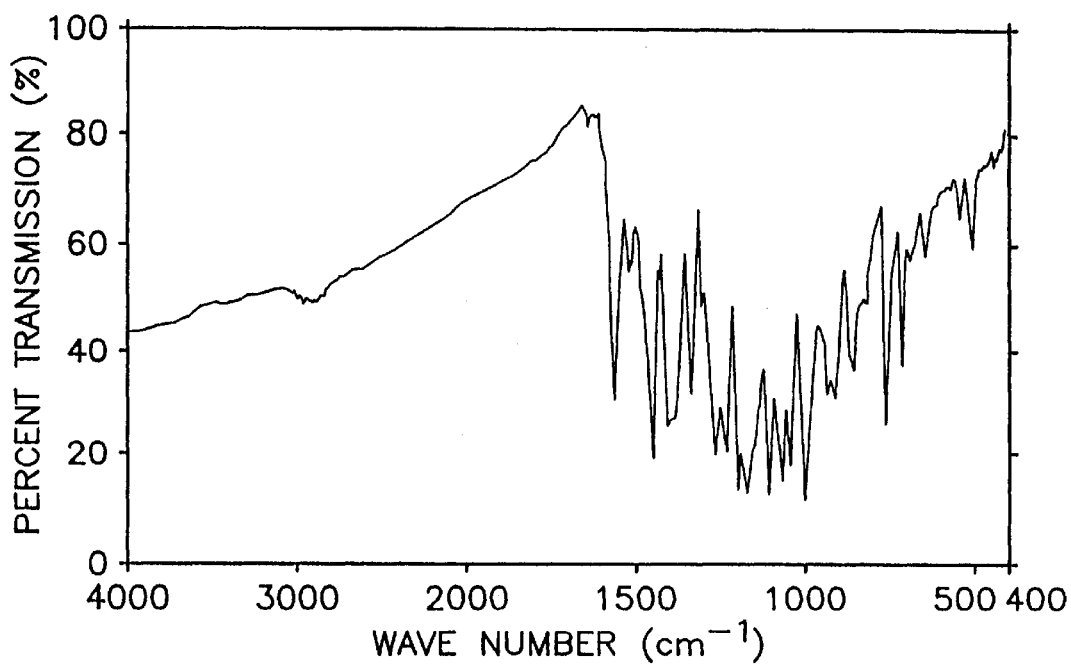
FIG. 1 is an FT-IR spectrum of the polymethine compound obtained in Example 1.

In the following, the present invention is described in detail.

[Polymethine Compound]

First, the polymethine compound according to the first aspect of the invention which is represented by the general formula (I) shown below is described.

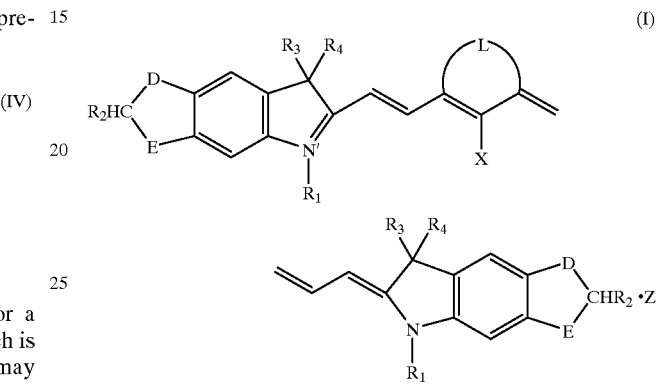

(I)

wherein $R_1$ represents an alkyl group, which may optionally be substituted, $R_2$ represents a hydrogen atom or a lower alkyl group, $R_3$ and $R_4$ each independently represents a lower alkyl group or $R_3$ and $R_4$ may combinedly form a cyclic structure, L is an alkylene group which is required for the formation of a cyclic structure and may optionally be substituted, one or more carbon atoms of which cyclic structure may be replaced by some other atom(s) or atomic group(s), D and E each independently represents an oxygen atom or a methine group, X represents a hydrogen or halogen atom or a substituted amino group, and Z represents a charge-neutralizing ion.

When $R_1$ is an unsubstituted alkyl group, said group is preferably a straight or branched alkyl group containing 1 to 18 carbon atoms, more preferably a straight or branched alkyl group containing 1 to 8 carbon atoms. Examples are methyl, ethyl, n-propyl, isopropyl, n-butyl, isobutyl, sec-butyl, n-pentyl, isopentyl, neopentyl, n-hexyl, isohexyl, sec-hexyl, 2-ethylbutyl, n-heptyl, isoheptyl, sec-heptyl, n-octyl, 2-ethylhexyl, n-decyl, n-dodecyl, n-pentadecyl and n-octadecyl, among others.

When $R_1$ is a substituted alkyl group, said group may be an alkoxyalkyl group, a sulfoalkyl group or a carboxyalkyl group, for instance. Said alkoxyalkyl group preferably contains 2 to 8 carbon atoms. As examples, there may be mentioned 2-methoxyethyl, 3-methoxypropyl, 4-methoxybutyl, 2-ethoxyethyl, 3-ethoxypropyl, 4-ethoxybutyl, 2-n-propoxyethyl, 2-isopropoxyethyl, 3-n-propoxypropyl, 4-n-propoxybutyl, 2'-methoxy-2-ethoxyethyl and 2-ethoxy-2-ethoxyethyl, among others.

Said sulfoalkyl group represented by $R_1$ is preferably a straight or branched sulfoalkyl group containing 1 to 18 carbon atoms, more preferably a straight or branched sulfoalkyl group containing 1 to 8 carbon atoms. It is preferred that at least one of these sulfoalkyl groups represented by $R_1$ be in the form of a salt with an alkali metal ion or an alkylammonium ion. As examples of such sulfoalkyl group, there may be mentioned 2-sulfoethyl, 3-sulfopropyl, 3-sulfobutyl, 4-sulfobutyl, 4-sulfo-3-methylbutyl, 2-(3-sulfopropoxy)ethyl, 2-hydroxy-3-sulfopropyl, 3-sulfo-2-(2-ethoxy)ethoxypropoxy, 5-sulfopentyl, 6-sulfohexyl, 8-sulfooctyl and 6-sulfo-2-ethylhexyl, among others, and these may be in the form of a salt with an alkali metal ion or an alkylammonium ion.

The carboxyalkyl group represented by $R_1$ is preferably a straight or branched carboxyalkyl group containing 2 to 18 carbon atoms, more preferably a straight or branched carboxyalkyl group containing 2 to 9 carbon atoms. It is preferred that at least one of these carboxyalkyl groups represented by $R_1$ be in the form of a salt with an alkali metal ion or an alkylammonium ion. As examples of such carboxyalkyl group, there may be mentioned 2-carboxyethyl, 3-carboxypropyl, 3-carboxybutyl, 4-carboxybutyl, 4-carboxy-3-methylbutyl, 2-(3-carboxypropoxy)ethyl, 2-hydroxy-3-carboxypropyl, 3-carboxy-2-(2-ethoxy)ethoxypropoxy, 5-carboxypentyl, 6-carboxyhexyl, 8-carboxyoctyl and 6-carboxy-2-ethylhexyl, among others, and these may be in the form of a salt with an alkali metal ion or an alkylammonium ion.

$R_2$ is a hydrogen atom or a lower alkyl group and, as the lower alkyl group, there may be mentioned methyl, ethyl, n-propyl, isopropyl, n-butyl, isobutyl and sec-butyl.

The lower alkyl group represented by each of $R_3$ and $R_4$ is, for example, methyl, ethyl, n-propyl, isopropyl, n-butyl, isobutyl or sec-butyl.

The ring structure formed by the combination of $R_3$ and $R_4$ together with the adjacent carbon atom is, for example, a cyclopropane, cyclobutane, cyclopentane, cyclohexane or cycloheptane ring. Among them, the cyclobutane, cyclopentane and cyclohexane rings are preferred.

X is preferably a hydrogen atom, a halogen atom such as F, Cl, Br or I, or ethylamino, phenylamino or diphenylamino. Particularly preferred are Cl, Br, diphenylamino and like substituted amino groups.

Z represents a charge-neutralizing ion and preferably is, for example, $F^-$, $Cl^-$, $Br^-$, $I^-$, $BrO_4^-$, $ClO_4^-$, benzenesulfonate, p-toluenesulfonate, naphthalenesulfonate, benzenedisulfonate, naphthalenedisulfonate, $CH_3SO_3^-$, $C_2H_5SO_3^-$, $C_3H_7SO_3^-$, $C_4H_9SO_3^-$, $C_5H_{11}SO_3^-$, $CF_3SO_3^-$, $C_2F_5SO_3^-$, $C_3F_7SO_3^-$, $C_4F_9SO_3^-$, $C_5F_{11}SO_3^-$, $CH_3CO_2^-$, $C_2H_5CO_2^-$, $C_3H_7CO_2^-$, $C_4H_9CO_2^-$, $C_5H_{11}CO_2^-$, $CF_3CO_2^-$, $C_2F_5CO_2^-$, $C_3F_7CO_2^-$, $C_4F_9CO_2^-$, $C_5F_{11}CO_2^-$, $BF_4^-$, $PF_6^-$, $SbF_6^-$, $Na^+$, $K^+$, triethylammonium ion or tetraethylammonium ion. Particularly preferred among these are $Cl^-$, $Br^-$, $I^-$, $ClO_4^-$, $BF_4^-$, $CF_3CO_2^-$, $PF_6^-$, $SbF_6^-$, $CH_3SO_3^-$, p-toluenesulfonate, $Na^+$, $K^+$ and triethylammonium ion.

$Z_1$ represents a charge-neutralizing ion and preferably is, for example, $F^-$, $Cl^-$, $Br^-$, $I^-$, $BrO_4^-$, $ClO_4^-$, benzenesulfonate, p-toluenesulfonate, naphthalenesulfonate, benzenedisulfonate, naphthalenedisulfonate, $CH_3SO_3^-$, $C_2H_5SO_3^-$, $C_3H_7SO_3^-$, $C_4H_9SO_3^-$, $C_5H_{11}SO_3^-$, $CF_3SO_3^-$, $C_2F_5SO_3^-$, $C_3F_7SO_3^-$, $C_4F_9SO_3^-$, $C_5F_{11}SO_3^-$, $CH_3CO_2^-$, $C_2H_5CO_2^-$, $C_3H_7CO_2^-$, $C_4H_9CO_2^-$, $C_5H_{11}CO_2^-$, $CF_3CO_2^-$, $C_2F_5CO_2^-$, $C_3F_7CO_2^-$, $C_4F_9CO_2^-$, $C_5F_{11}CO_2^-$, $BF_4^-$, $PF_6^-$, or $SbF_6^-$. Particularly preferred among these are $Cl^-$, $Br^-$, $I^-$, $ClO_4^-$, p-toluenesulfonate, $CH_3SO_3^-$, $BF_4^-$, $CF_3CO_2^-$, $PF_6^-$ and $SbF_6^-$.

L is a substituted or unsubstituted alkylene group, preferably containing 2 to 4 carbon atoms, and forms a ring together with the three carbon atoms, namely the carbon atom bearing X and both carbon atoms adjacent thereto. L is preferably ethylene, propylene, butylene, 2-oxapropylene, 2-thiapropylene, 2-azapropylene, 2-methylpropylene or 2-tert-butylpropylene, more preferably ethylene, propylene or butylene.

Preferred examples of the polymethine compound of the present invention as represented by the general formula (I) are shown below without any intention of limiting the scope of said compound.

Compound (1)

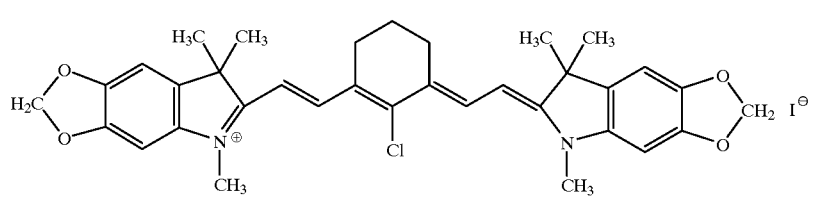

Compound (2)

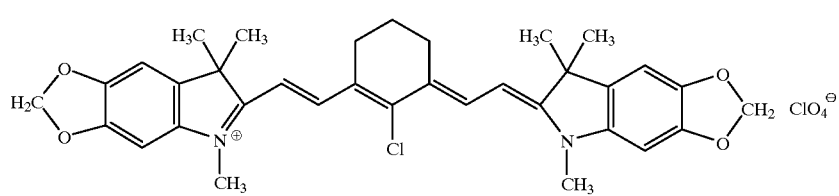

Compound (3)

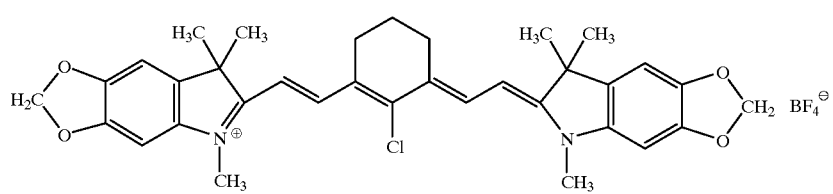

-continued
Compound (4)
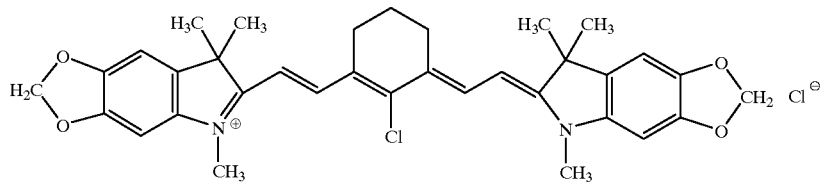
Compound (5)
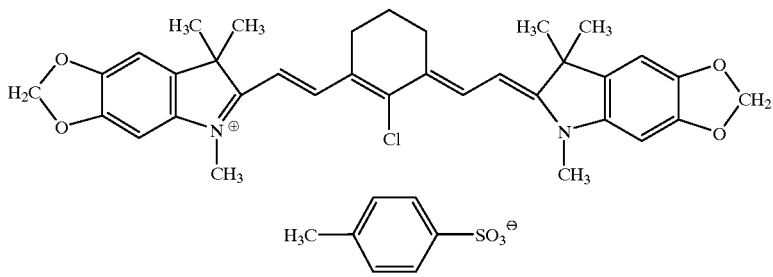
Compound (6)
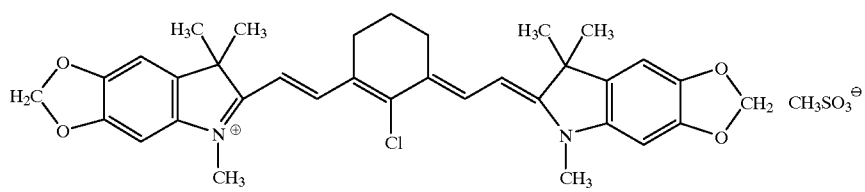
Compound (7)
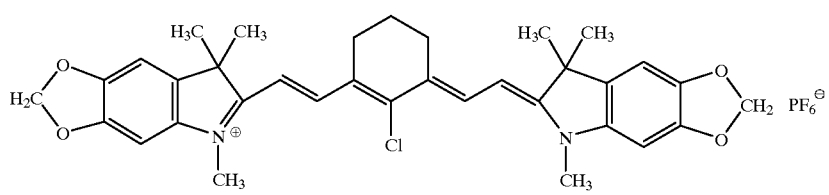
Compound (8)
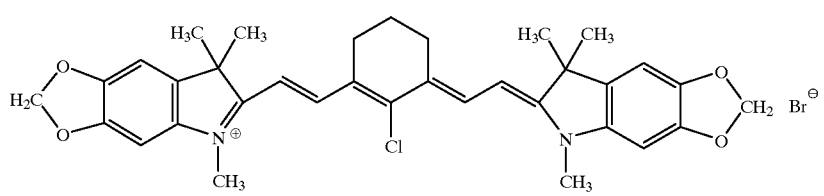
Compound (9)
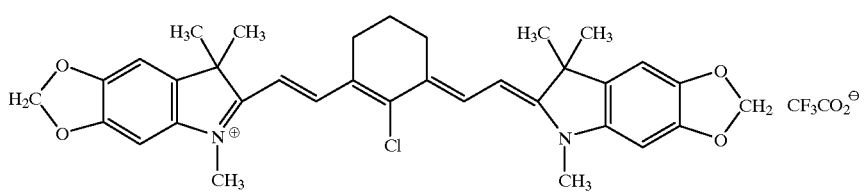
Compound (10)
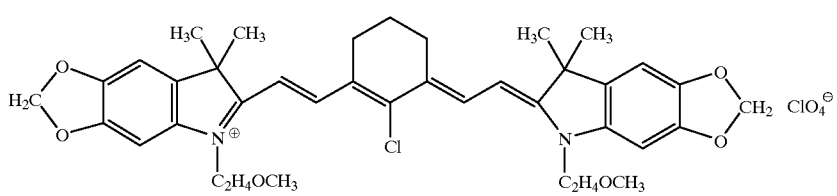

-continued
Compound (11)
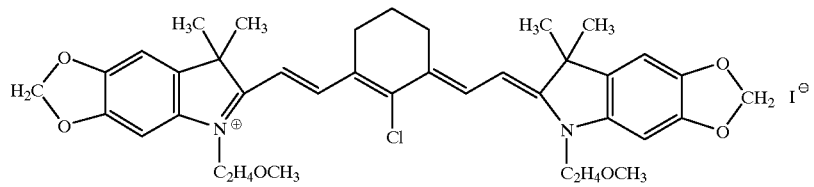
Compound (12)
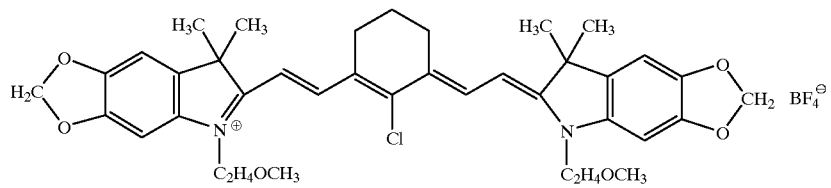
Compound (13)
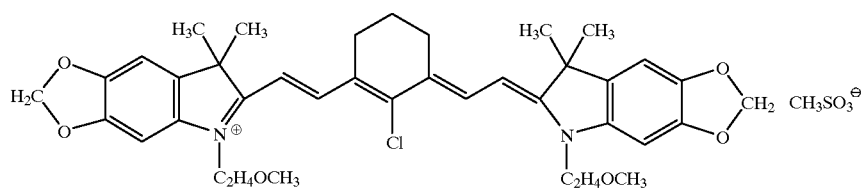
Compound (14)
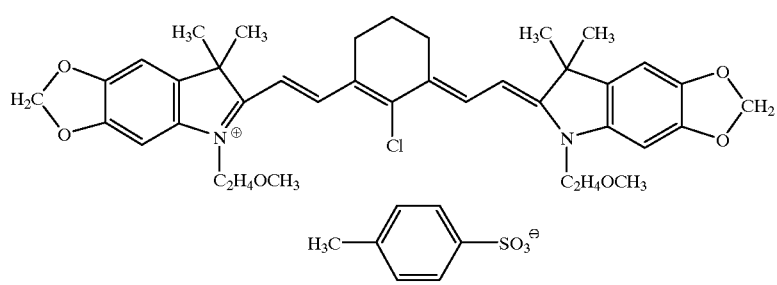
Compound (15)
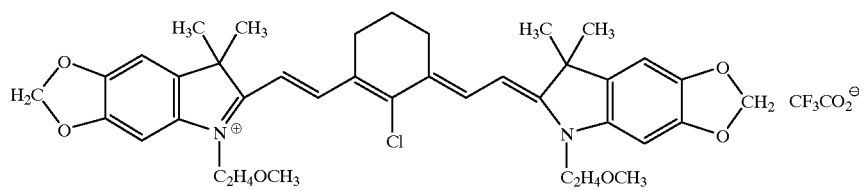
Compound (16)
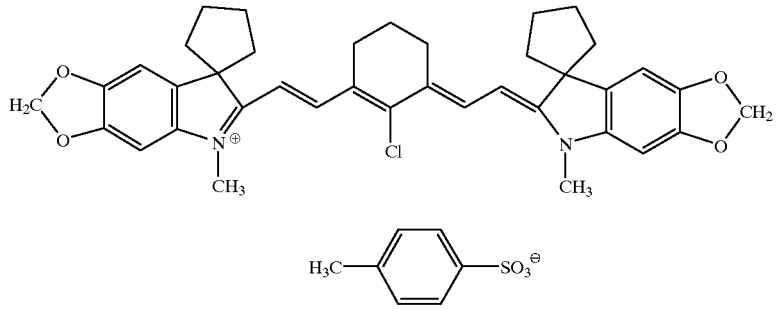

-continued
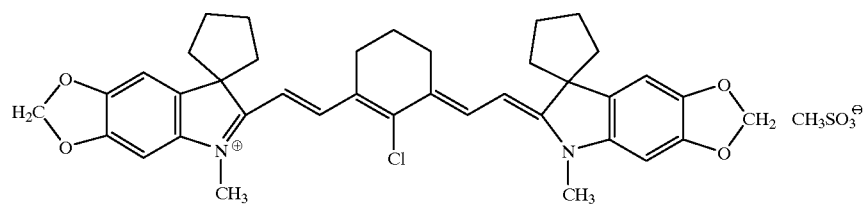
Compound (17)
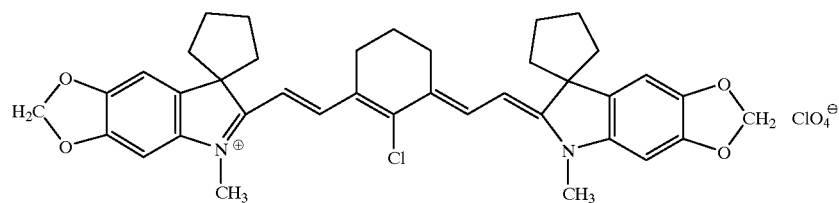
Compound (18)
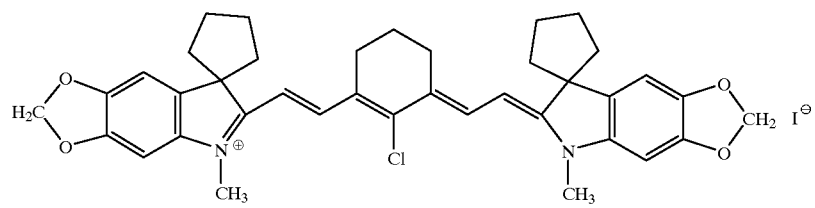
Compound (19)
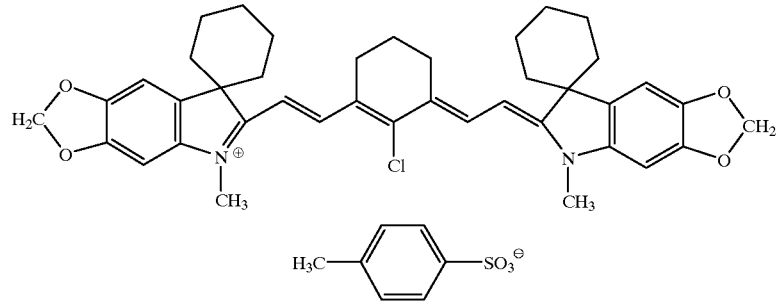
Compound (20)
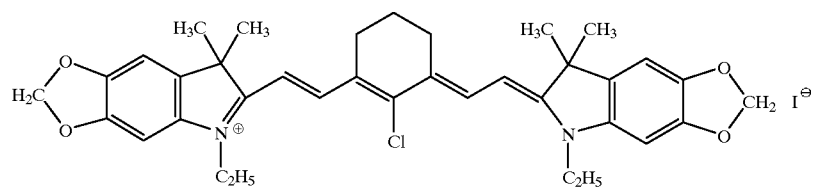
Compound (21)
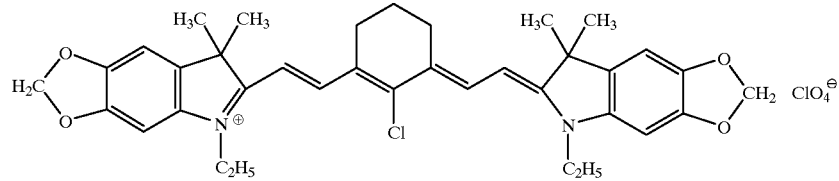
Compound (22)

-continued
Compound (23)
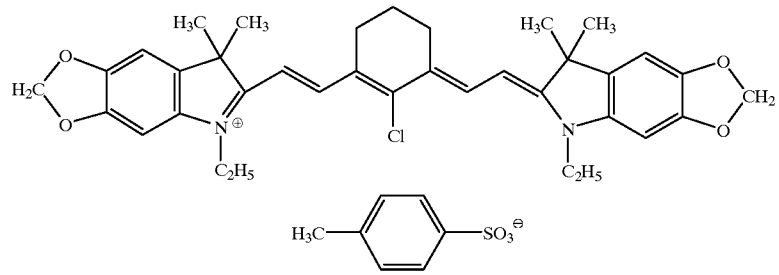
Compound (24)
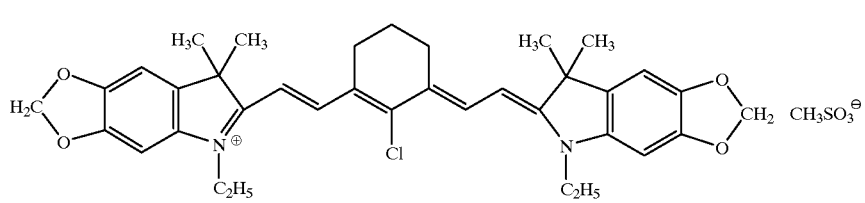
Compound (25)
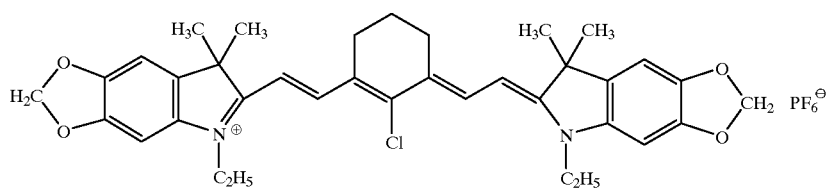
Compound (26)
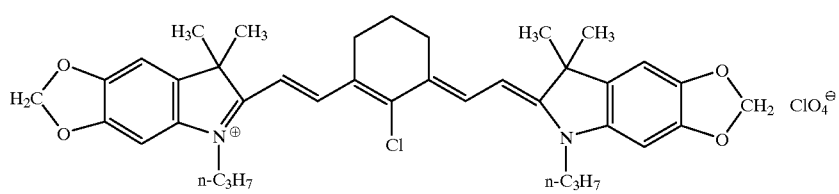
Compound (27)
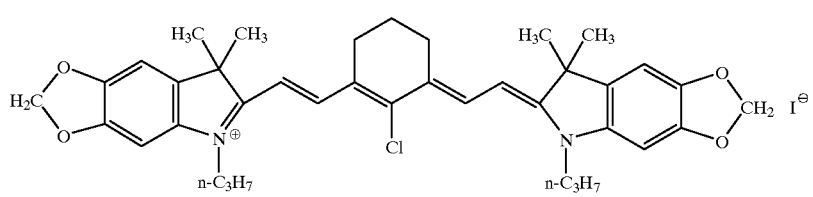
Compound (28)
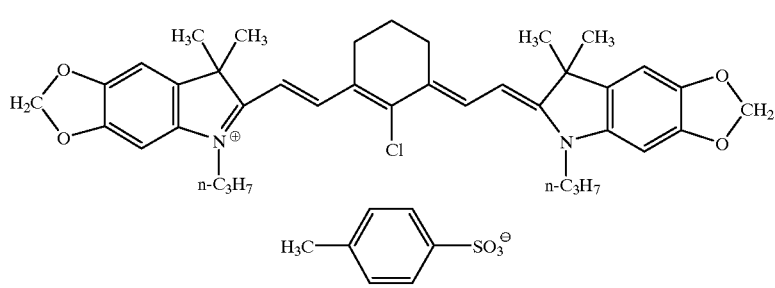

-continued
Compound (29)
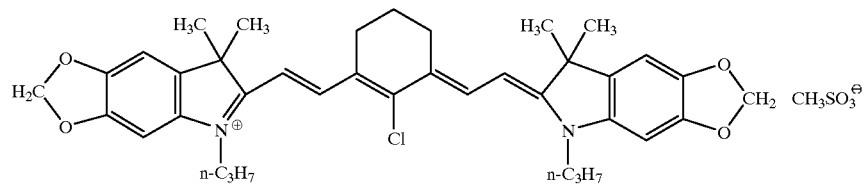
Compound (30)
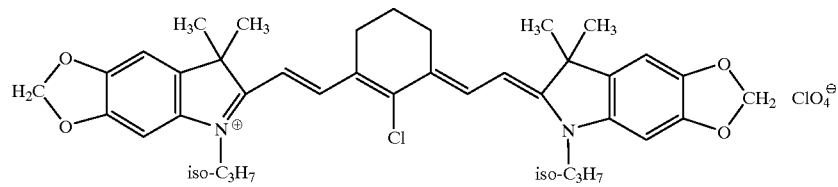
Compound (31)
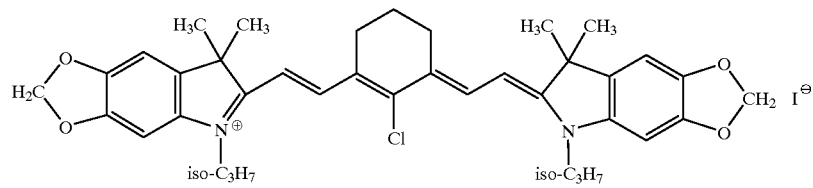
Compound (32)
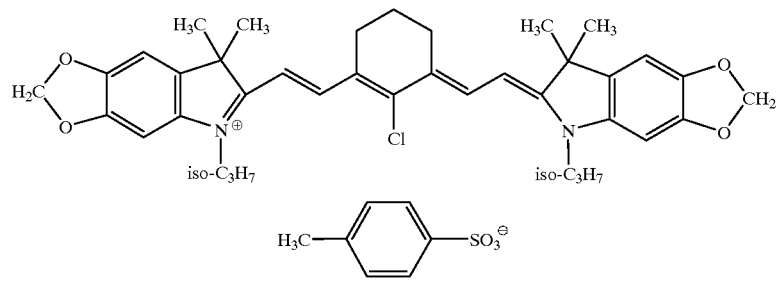
Compound (33)
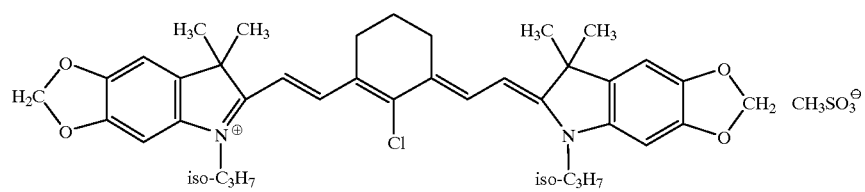
Compound (34)
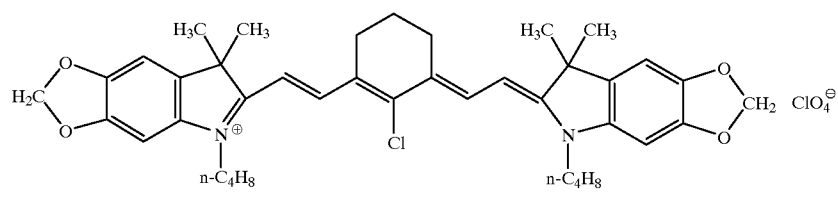
Compound (35)
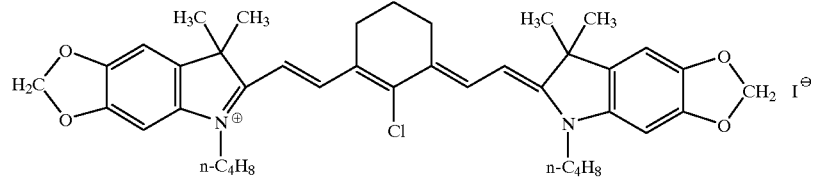

-continued
Compound (36)
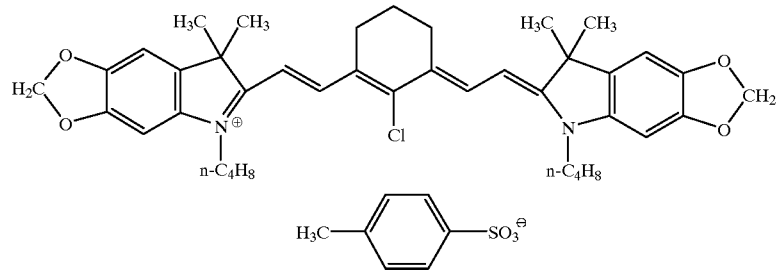
Compound (37)
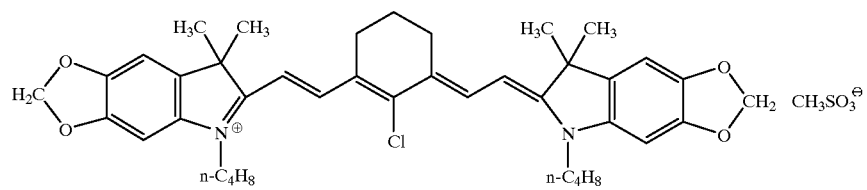
Compound (38)
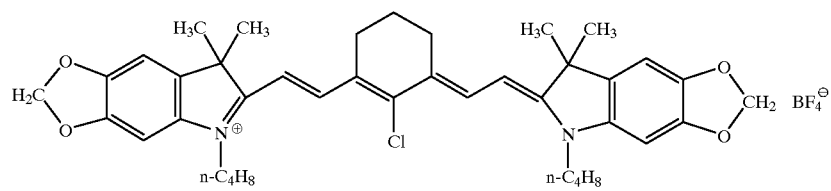
Compound (39)
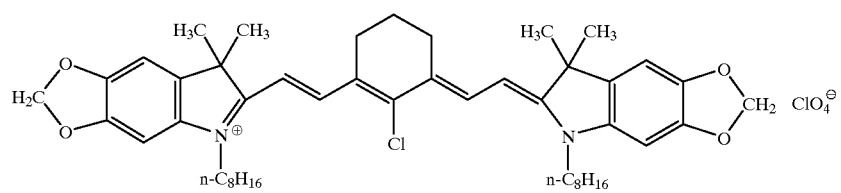
Compound (40)
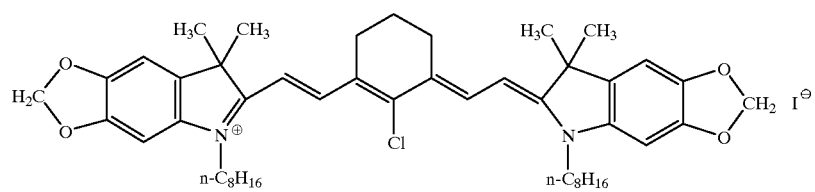
Compound (41)
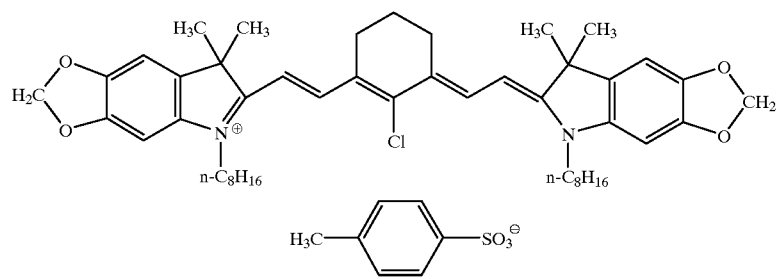

-continued
Compound (42)
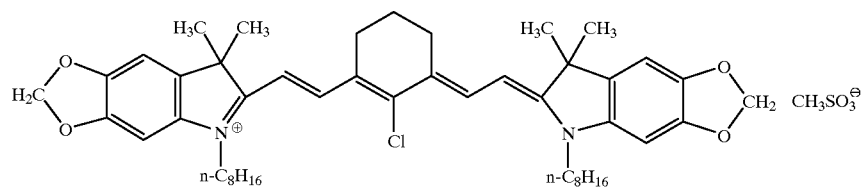
Compound (43)
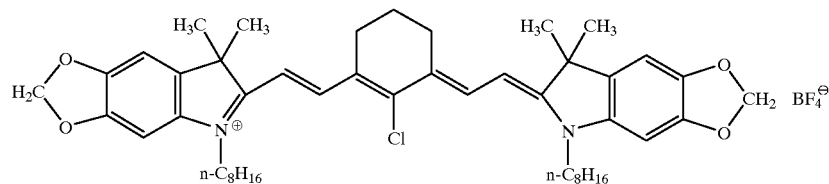
Compound (44)
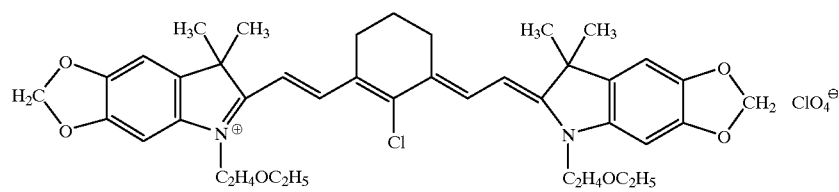
Compound (45)
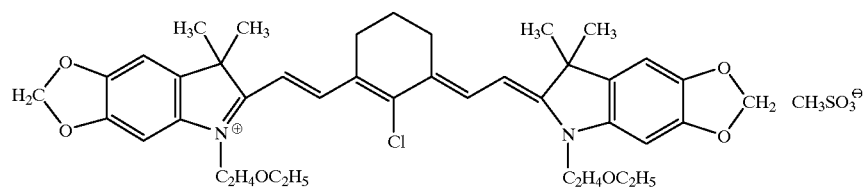
Compound (46)
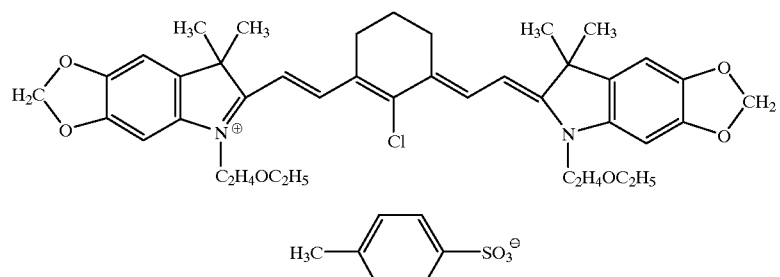
Compound (47)
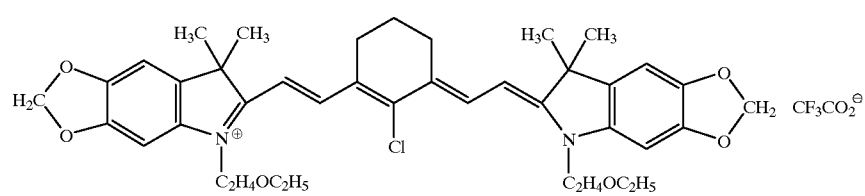
Compound (48)
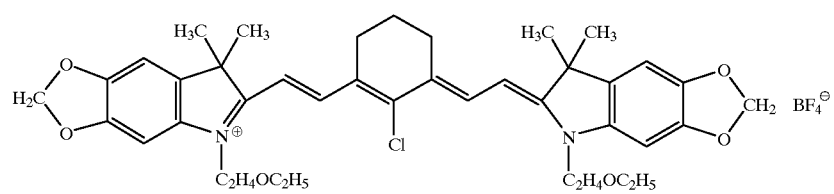

-continued
Compound (49)
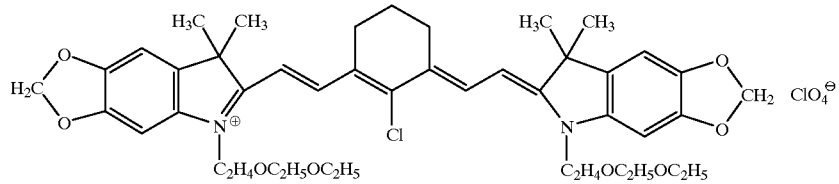
Compound (50)
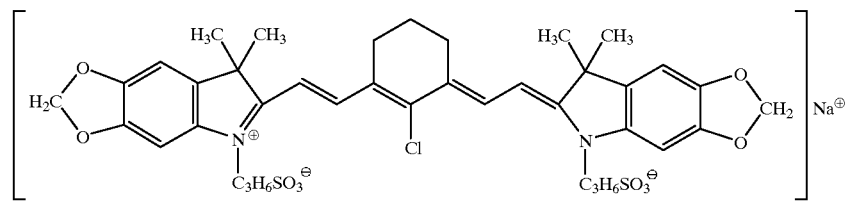
Compound (51)
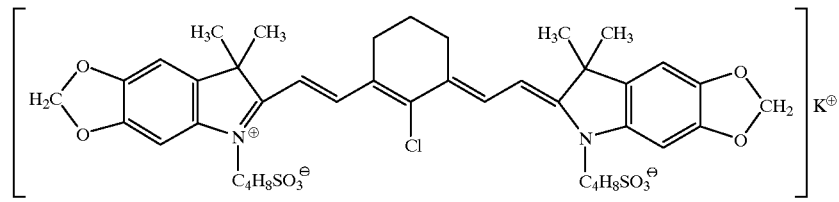
Compound (52)
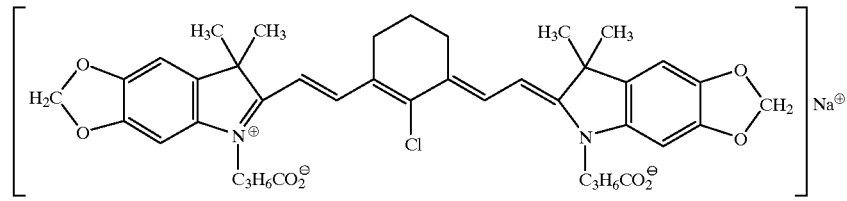
Compound (53)
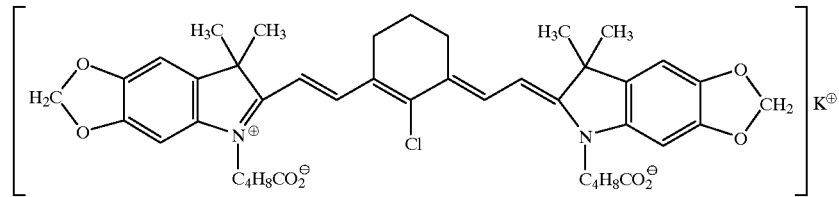
Compound (54)
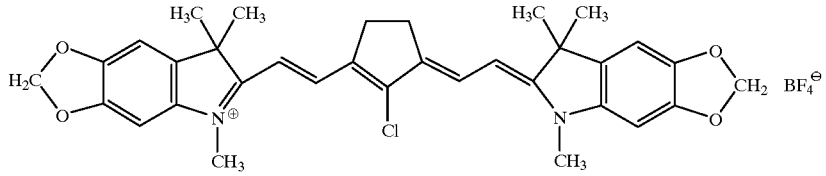
Compound (55)
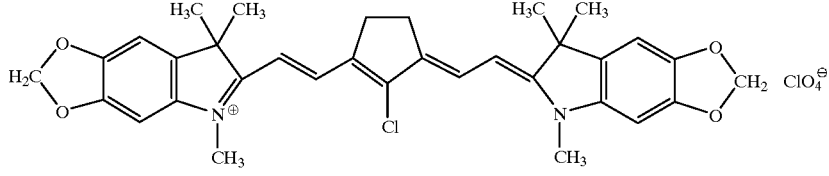

-continued
Compound (56)
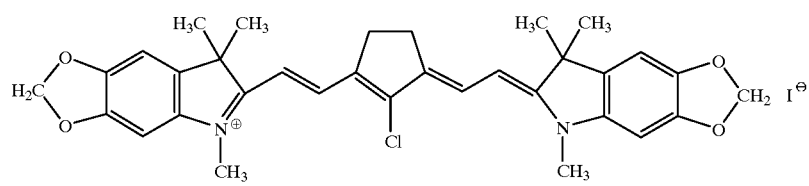
Compound (57)
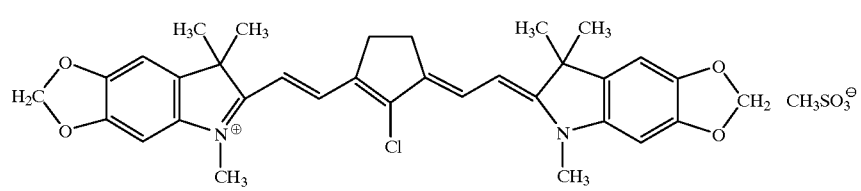
Compound (58)
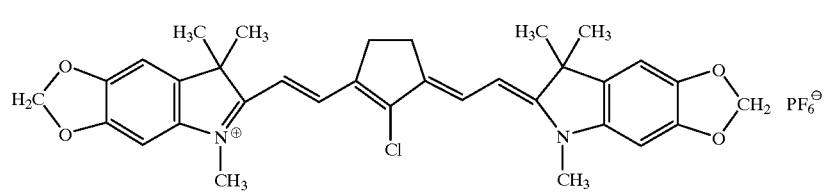
Compound (59)
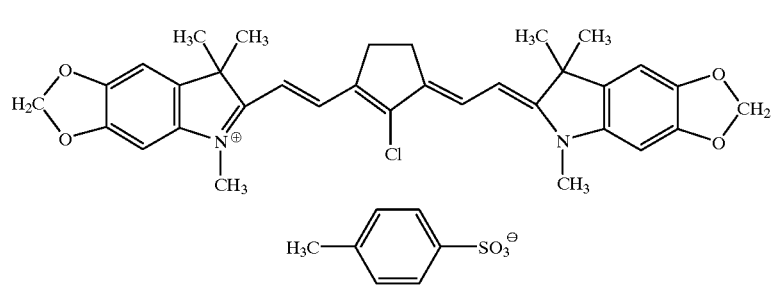
Compound (60)
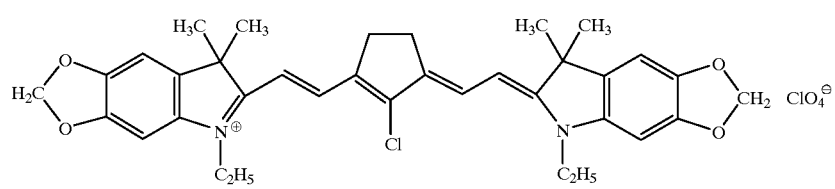
Compound (61)
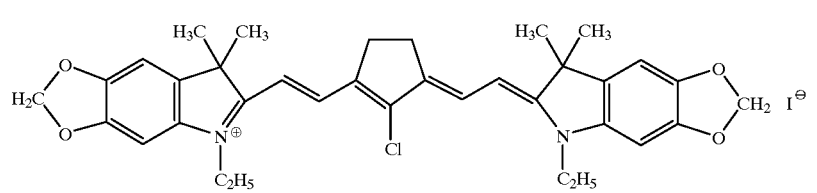
Compound (62)
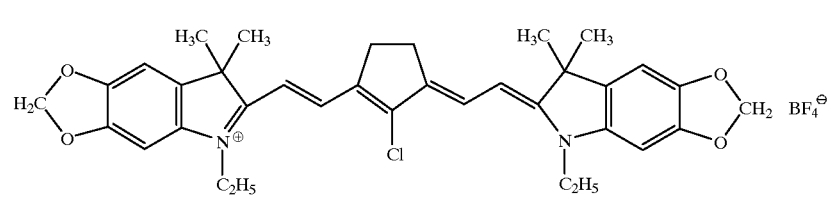

-continued
Compound (63)
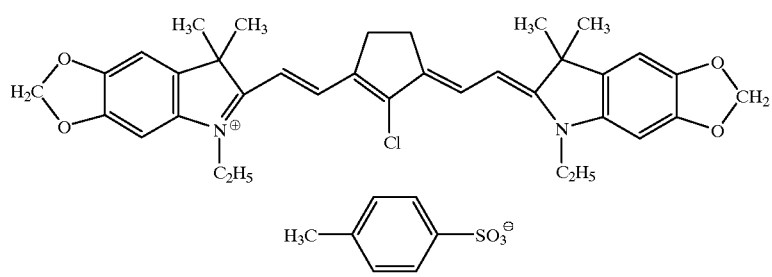
Compound (64)
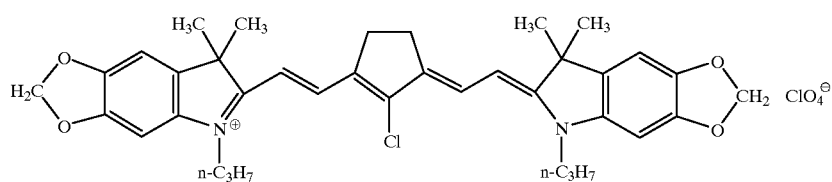
Compound (65)
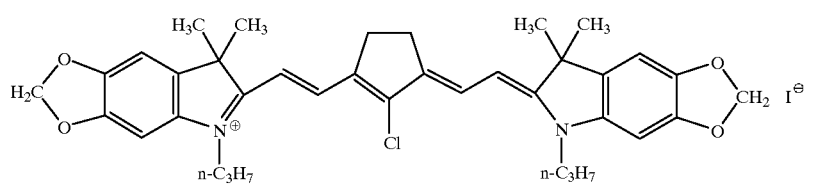
Compound (66)
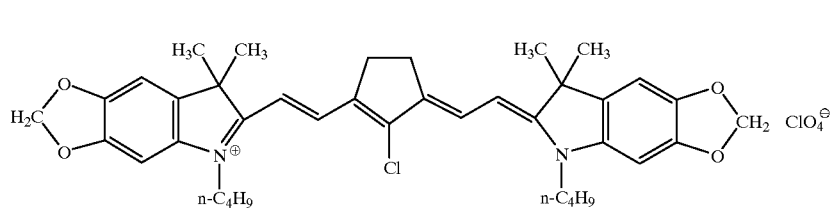
Compound (67)
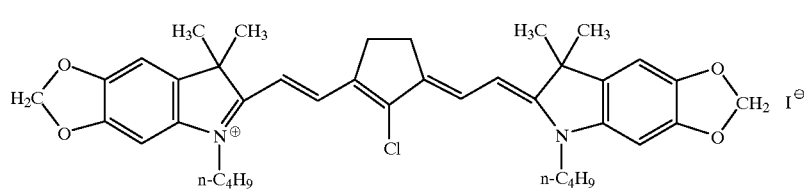
Compound (68)
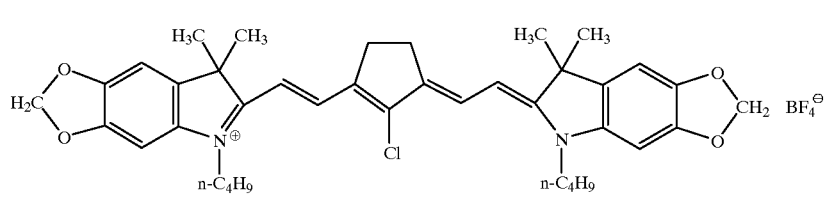
Compound (69)
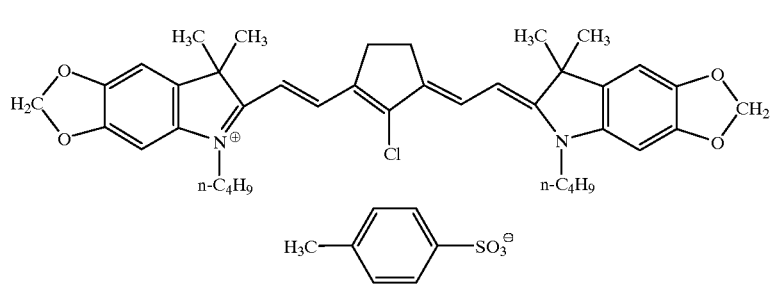

Compound (70)
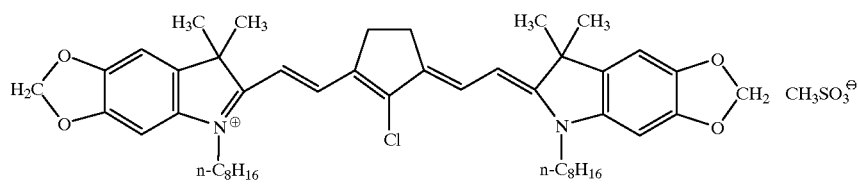
Compound (71)
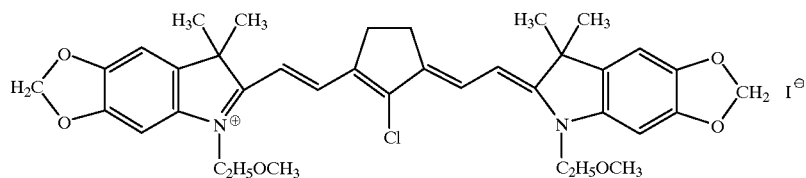
Compound (72)
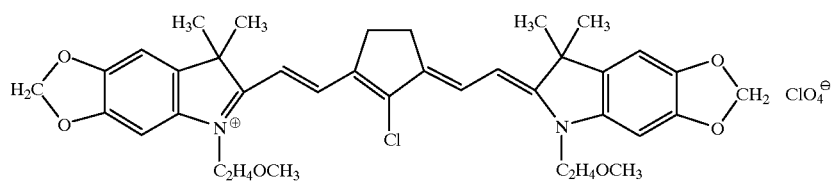
Compound (73)
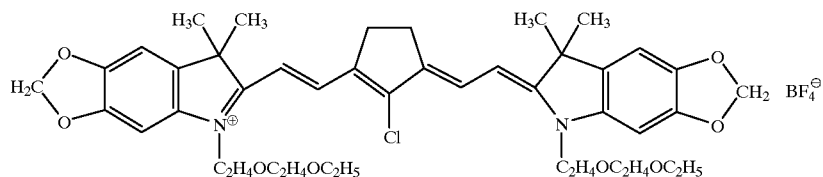
Compound (74)
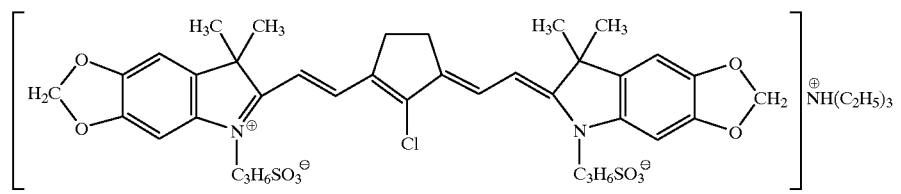
Compound (75)
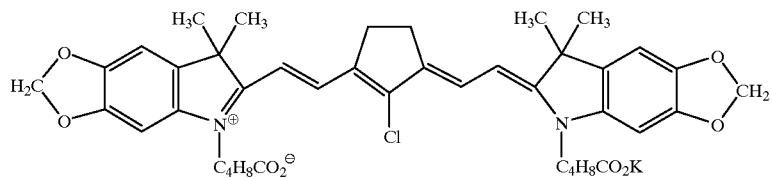
Compound (76)
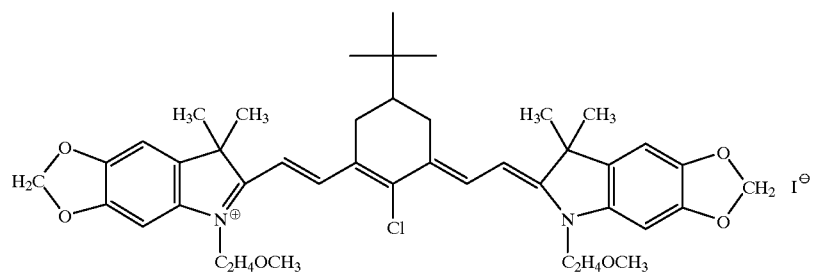

-continued
Compound (77)
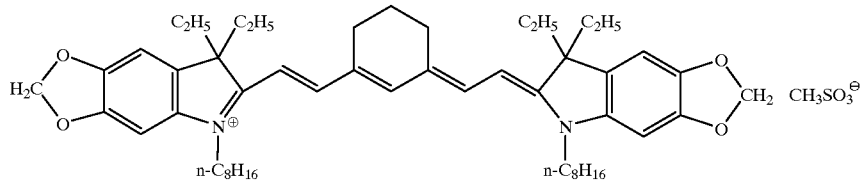
Compound (78)
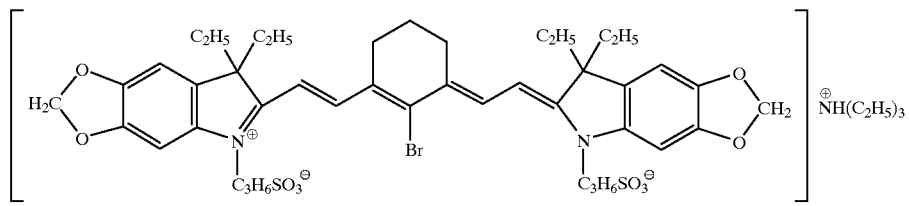
Compound (79)
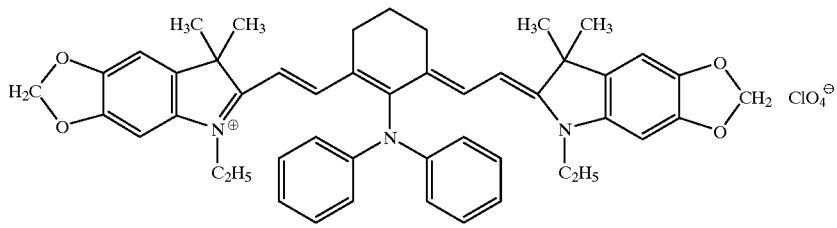
Compound (80)
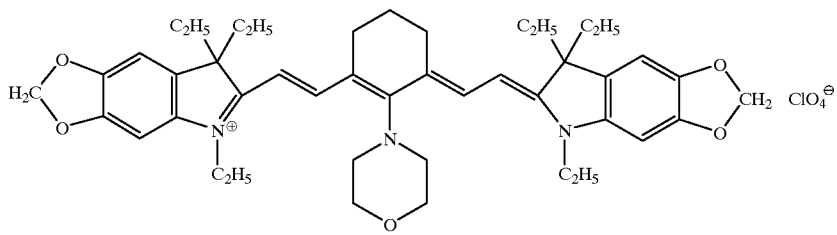
Compound (81)
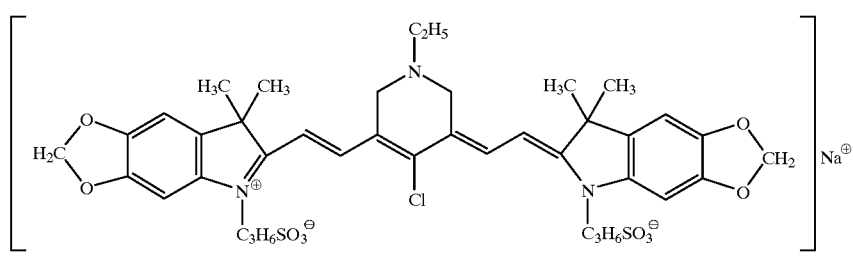
Compound (82)
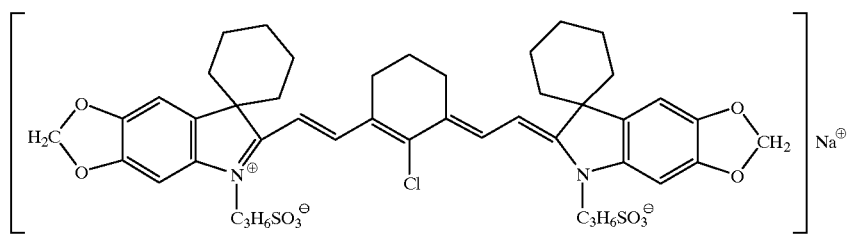

-continued
Compound (83)
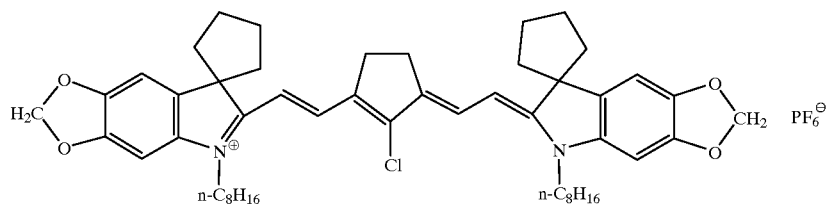
Compound (84)
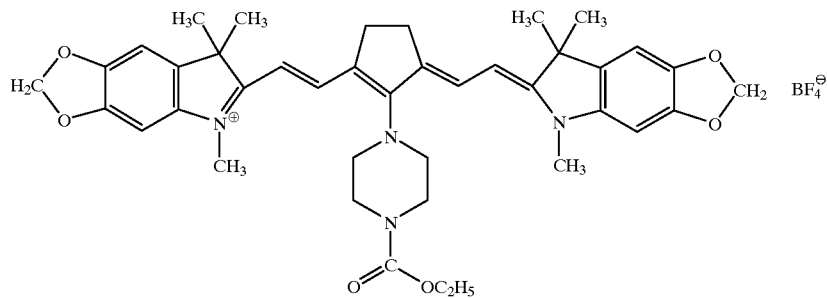
Compound (85)
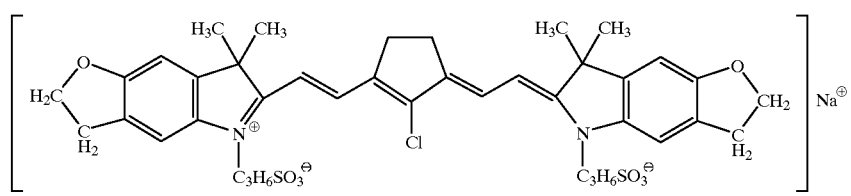
Compound (86)
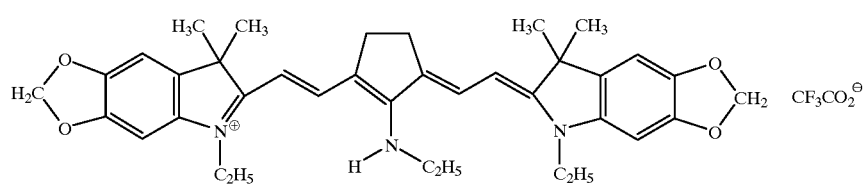
Compound (87)
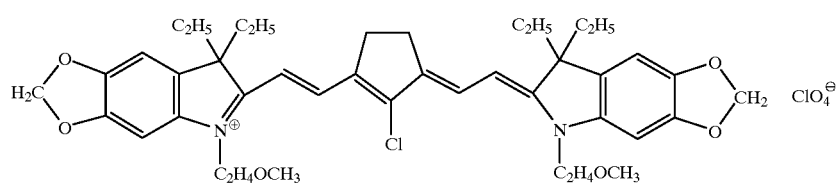
Compound (88)
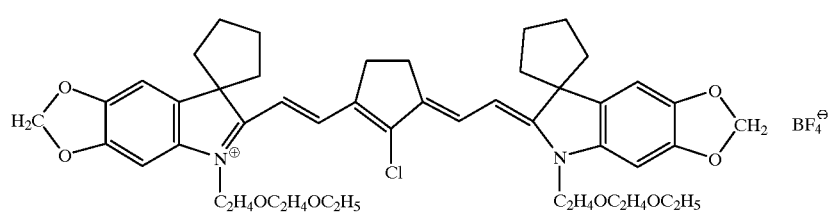
Compound (89)
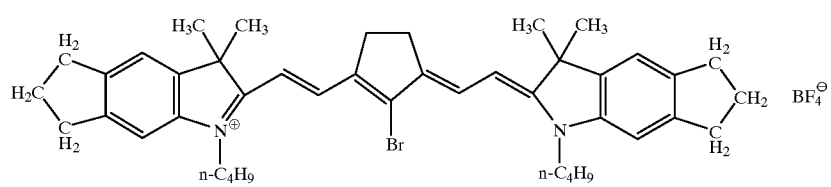

-continued
Compound (90)
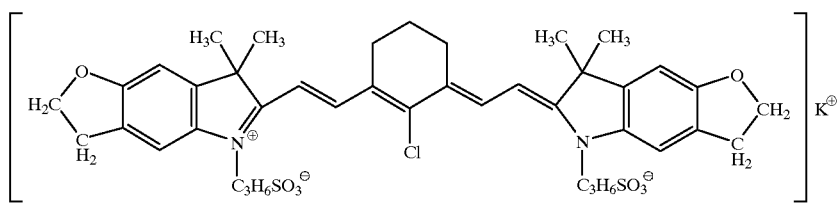
Compound (91)
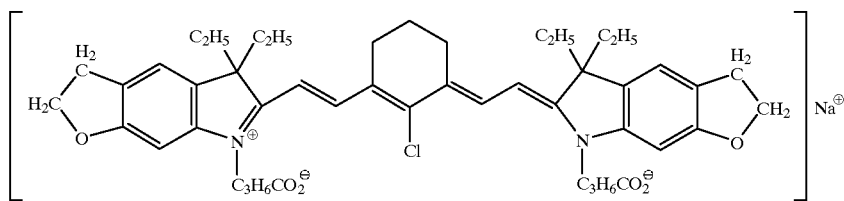
Compound (92)
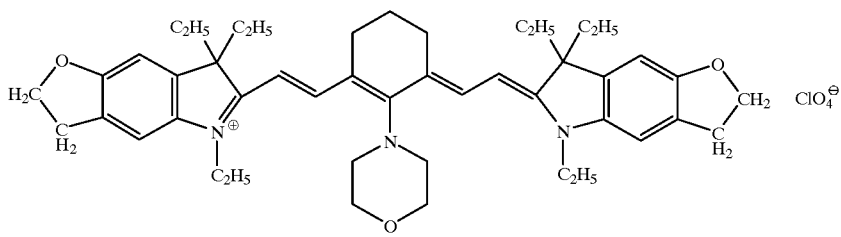
Compound (93)
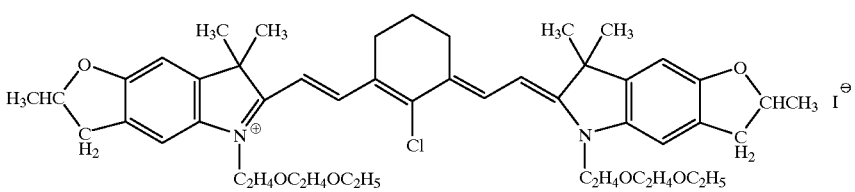
Compound (94)
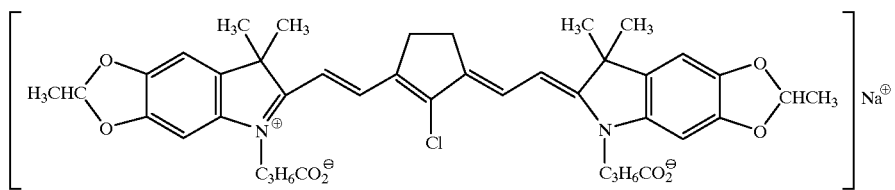
Compound (95)
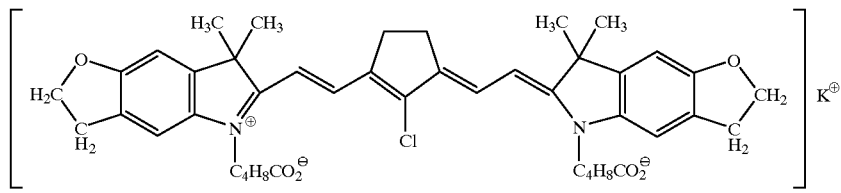
Compound (96)
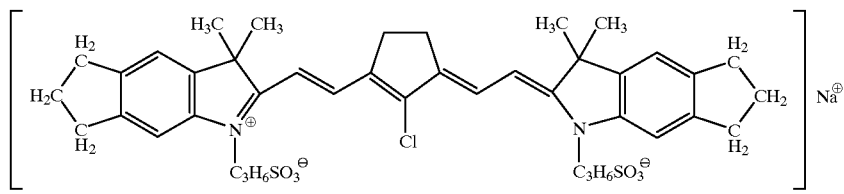

-continued

Compound (97)

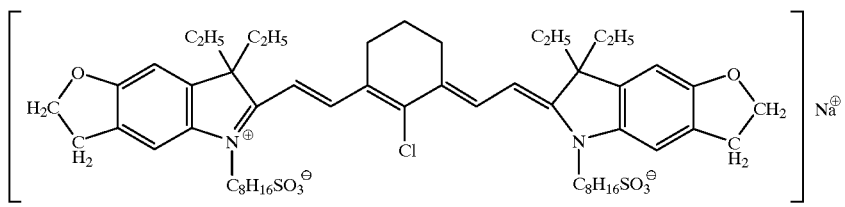

Compound (98)

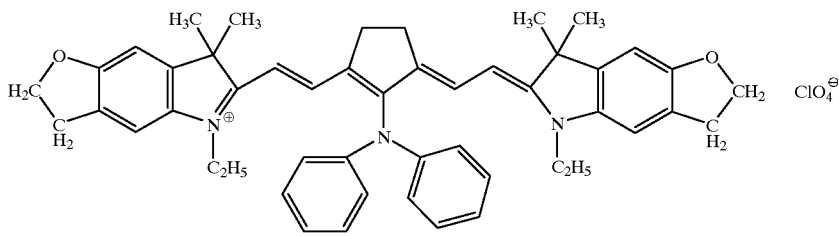

Compound (99)

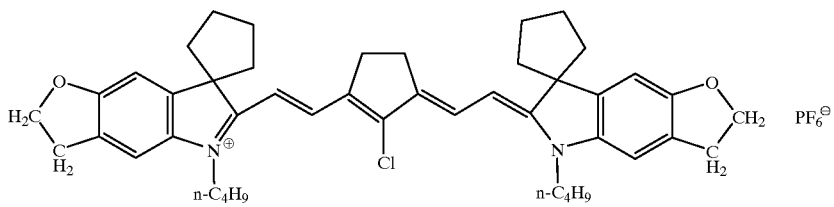

Among the compounds (1) to (99) given above as specific examples, those compounds which are represented by the general formula (V) shown below may be represented also by the general formula (VI) given below.

In the above formulas, $R_1$ to $R_4$, D, E, X and L are as defined above and M represents Na, K or triethylammonium. Thus, the specific compound (50), for instance, may be represented alternatively as follows:

(V)

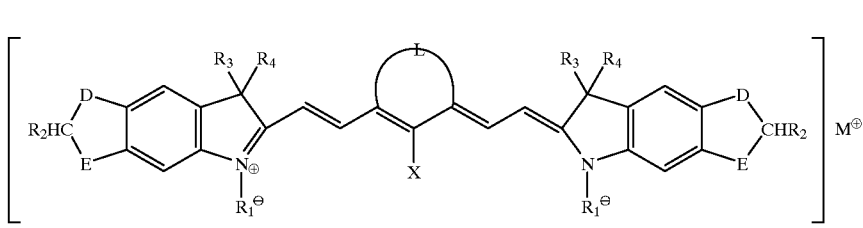

(VI)

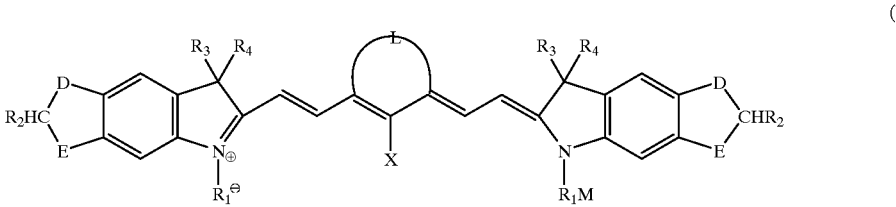

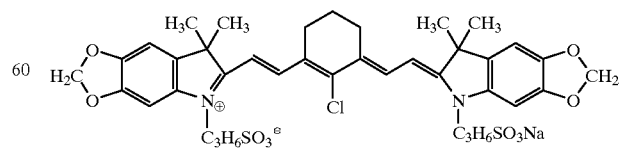

[Method of Producing the Polymethine Compound]

The polymethine compound of the present invention is produced, for example, by subjecting an indolenium compound represented by the general formula (II) and a diformyl compound represented by the general formula (III) or a dianil compound represented by the general formula (IV) to condensation reaction in the presence of a fatty acid salt in a dehydrating organic acid.

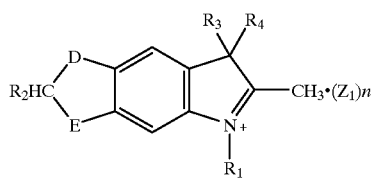

(II)

(In the above formula, $R_1$ to $R_4$, D, E and $Z_1$ are as defined above.)

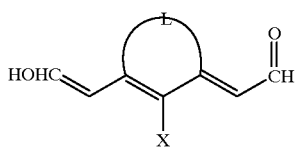

(III)

(In the above formula, X and L are as defined above.)

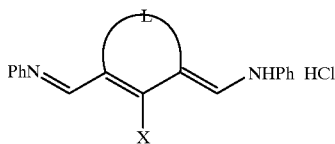

(IV)

(In the above formula, X and L are as defined above.)

In the above condensation reaction, the fatty acid salt is, for example, sodium acetate, potassium acetate, calcium acetate, sodium propionate, potassium propionate or the like.

Such fatty acid salt is used generally in an amount of about 0.1 to 5 moles, preferably about 0.5 to 2 moles, per mole of the compound of general formula (III).

As the dehydrating organic acid, there may be mentioned acetic anhydride, propionic anhydride, butyric anhydride, γ-butyrolactone and the like.

Such dehydrating organic acid is used generally in an amount of about 10 to 100 moles, preferably about 20 to 50 moles, per mole of the compound of general formula (II).

As for the proportion of the compound of general formula (II) to the compound of general formula (III) or (IV), the latter is used generally in an amount of about 0.2 to 1.5 moles, preferably about 0.4 to 0.7 moles, per mole of the former.

The above reaction can proceed generally at about 10 to 150° C., preferably at room temperature to 120° C., and will be complete generally in several minutes to about 3 hours.

After the reaction, the desired product can be readily isolated from the reaction mixture, for example, by pouring a poor solvent, such as water, methanol, ethanol, n-propanol, isopropanol or n-butanol, into said mixture or discharging said mixture into a poor solvent such as water, methanol, ethanol, n-propanol, isopropanol or n-butanol. The product can be readily purified in the conventional manner, for example by recrystallization, column separation and/or other appropriate means.

The compound represented by the general formula (II) can be synthesized, for example, by the method described in JP Kokai H02-229865 etc.

The diformyl compound represented by the general formula (III) can be synthesized, for example, by the method described in Journal of Organic Chemistry, 42, 885–888 (1977) etc. The dianil compound represented by the general formula (IV) can be readily synthesized by reacting the diformyl compound of general formula (III) with aniline hydrochloride.

[Near Infrared Absorber]

The near infrared absorber of the present invention may contain a binder resin in addition to the polymethine compound of general formula (I).

The near infrared absorber may comprise one or more of various known near infrared absorbers in combination with the polymethine compound of general formula (I) within the limits beyond which the object of the present invention cannot be fulfilled.

As the known near infrared absorbers which can be used in combination, there may be mentioned carbon black, aniline black and like pigments, those polymethine dyes (cyanine dyes), phthalocyanine dyes, dithiol metal complex dyes, naphthoquinone and anthraquinone dyes, triphenylmethane (-like) dyes, aluminum, diimmonium dyes and so forth which are described in "Kagaku Kogyo (Chemical Industry)", May, 1986, pages 45–51 under the title "Near infrared absorbing dyes" or in the monograph "Development and Market Trends of Functional Dyes for the Nineties", publsihed by CMC, 1990, Chapter 2, Paragraphs 2 and 3, and, further, azo dyes, indoaniline metal complex dyes, intermolecular CT dyes and other pigments and dyes.

The binder resin is not particularly restricted but includes, among others, homopolymers and copolymers based on acrylic acid, methacrylic acid, acrylic esters, methacrylic esters and other acrylic monomers, methylcellulose, ethylcellulose, cellulose acetate and other cellulosic polymers, polystyrene, vinyl chloride-vinyl acetate copolymers, polyvinylpyrrolidone, polyvinyl butyral, polyvinyl alcohol and other vinyl polymers and copolymers of vinyl compounds, polyesters, polyamides and other condensate polymers, butadiene-styrene copolymers and other rubber-like thermoplastic polymers, and polymers obtained by polymerization and crosslinking of epoxy compounds or like photopolymerizable compounds.

When the near infrared absorber of the present invention is used in optical recording materials such as optical cards, they can be made by applying a solution of the near infrared absorber in an organic solvent to substrates made of glass or a plastic resin, for instance, by any of the various techniques so far explored, for example by spin coating. The resin for use in preparing said substrates is not particularly restricted but includes, among others, acrylic resins, polyethylene resins, vinyl chloride resins, vinylidene chloride resins, polycarbonate resins and the like. The solvent to be used in spin coating is not particularly restricted but includes, among others, hydrocarbons, halogenated hydrocarbons, ethers, ketones, alcohols and cellosolves and, among them, alcohols, such as methanol, ethanol and propanol, and cellosolve solvents, such as methylcellosolve and ethylcellosolve, are particularly preferred.

When the near infrared absorber of the present invention is used in near infrared absorbing filters, infrared blocking materials or films for agricultural use, these can be produced by admixing the near infrared absorber with a plastic resin, if necessary together with an organic solvent, and molding the mixture into sheets or films by any of the various techniques so far explored, for example by injection molding or casting. The resin to be used is not particularly restricted but includes, among others, acrylic resins, polyethylene resins, vinyl chloride resins, vinylidene chloride resins, polycarbonate resins and the like. The solvent to be used is not particularly restricted but includes, among others, hydrocarbons, halogenated hydrocarbons, ethers, ketones, alcohols and cellosolves and, among them, alcohols, such as methanol, ethanol and propanol, and cellosolve solvents, such as methylcellosolve and ethylcellosolve, are particularly preferred.

When the near infrared absorber of the present invention is used in laser thermal transfer recording materials, laser heat-sensitive recording materials and like recording materials, a chromogen component or a colorant component, for instance, may be incorporated in the near infrared absorber, or a layer containing a chromogen component or a colorant component, for instance, may be provided separately. Usable as the chromogen or colorant component are those substances capable of forming images as a result of a physical or chemical change due to heat which have so far been explored in various ways, for example subliming dyes or pigments, electron-donating dye precursors combined with an electron-accepting compound, and polymerizing polymers. Thus, for example, the colorant component in laser thermal transfer recording materials is not particularly restricted but includes inorganic pigments such as titanium dioxide, carbon black, zinc oxide, Prussian blue, cadmium sulfide, iron oxide, and lead, zinc, barium and calcium chromates and organic pigments such as azo, thioindigo, anthraquinone, anthanthrone, triphenodioxane, phthalocyanine, quinacridone and other type ones. As dyes, there may be mentioned acid dyes, direct dyes, disperse dyes, oil colors, metal-containing oil colors, and so forth.

The chromogen component for use in laser heat-sensitive recording materials is not particularly restricted but may be any of those conventionally used in heat-sensitive recording materials. As the electron-donating dye precursors, namely substances capable of donating an electron or electrons and accepting a proton or protons from an acid or acids or the like to thereby develop a color, use may be made of those compounds having such a partial skeleton as a lactone, lactam, sultone, spiropiran, ester or amide structure and capable of undergoing ring opening or cleavage of such partial skeleton upon contact with an electron-accepting compound. Thus, for example, there may be mentioned triphenylmethane compounds, fluoran compounds, phenothiazine compounds, indolylphthalide compounds, lueco auramine compounds, rhodamine lactam compounds, triphenylmethane compounds, triazene compounds, spiropyran compounds and fluorene compounds, among others. As the electron-accepting compound, there may be mentioned phenolic compounds, organic acids or salts thereof, and hydroxybenzoic acid esters, among others.

[Original Plate for Direct Plate Making]

The polymethine compound of the present invention can judiciously be used as a near infrared absorber in original plates for direct plate making. The original plates for direct plate making comprise a light-to-heat conversion layer provided on a substrate. A silicone rubber layer and/or a protective layer may be provided on the light-to-heat conversion layer.

The components constituting the light-to-heat conversion layer include, in addition to the polymethine compound of the present invention, an image forming component, a binder resin and so forth. Alternatively, a layer containing an image forming component may be provided on the light-to-heat conversion layer.

Useful as the image forming component are those which can form images as a result of a physical or chemical change due to heat and which have so far been explored in various ways. Thus, for example, there may be mentioned, without any particular restriction, those containing a microencapsulated heat-fusible substance and a binder resin, among others, as disclosed in JP Kokai H03-108588, those containing a blocked isocyanate, among others, together with an active hydrogen-containing binder on a substrate having a hydrophilic surface as disclosed in JP Kokai S62-164049, those containing a microencapsulated lipophilic component and a hydrophilic binder polymer, among others, as disclosed in JP Kokai H07-1849, those containing an acid precursor, a vinyl ether group-containing compound and an alkali-soluble resin, for instance, as disclosed in JP Kokai H08-220752, those containing a hydroxy-containing macromolecular compound and an o-naphthoquinone diazide compound, among others, as disclosed in JP Kokai H09-5993, those containing nitrocellulose, among others, as disclosed in JP Kokai H09-131977, and those containing a polymerization initiator and an ethylenically unsaturated monomer, oligomer or macromonomer, among others, as disclosed in JP Kokai H09-14626. Optionally, a silicone rubber layer may be laid on the light-to-heat conversion layer (photosensitive or heat-sensitive layer) so that said silicone rubber layer may be subjected to firm adhesion or peeling off after exposure to thereby form image areas, as disclosed in JP Kokai H09-80745, JP Kokai H09-131977, JP Kokai H09-146264 and elsewhere.

The binder resin to be used in the light-to-heat conversion layer is not particularly restricted but includes, among others, homopolymers or copolymers of acrylic acid, methacrylic acid, acrylic esters, methacrylic esters or like acrylic monomers, methylcellulose, ethylcellulose, cellulose acetate and like cellulosic polymers, polystyrene, vinyl chloride-vinyl acetate copolymers, polyvinylpyrrolidone, polyvinyl butyral, polyvinyl alcohol and like vinyl polymers and copolymers of vinyl compounds, polyesters, polyamides and like polycondesates, butadiene-styrene copolymers and like rubber-like thermoplastic polymers, and polymers obtained by polymerization and crosslinking of epoxy compounds or like photopolymerizable compounds.

The original plate for plate making as provided by the present invention should be flexible so that it may be set on a conventional printing press and, at the same time, it should be able to endure the pressure applied at the time of printing. Thus, as the substrate or support member to be used, there may be mentioned, among others, paper, plastic-laminated (e.g. polyethylene-, polypropylene-, or polystyrene-laminated) paper, sheets of a metal such as aluminum (inclusive of aluminum alloys), zinc or copper, films made of a plastic such as cellulose diacetate, cellulose triacetate, cellulose butyrate, polyethylene terephthalate, polyethylene, polystyrene, polypropylene, polycarbonate or polyvinyl acetal, and the like. Typical among them are coated paper, sheets of a metal such as aluminum, plastic films such as polyethylene terephthalate films, rubber sheets, and composite materials produced from such materials. Preferred are aluminum sheets, aluminum-containing alloy sheets and plastic films. The substrate has a thickness of 25 $\mu$m to 3 mm, preferably 100 $\mu$m to 500 $\mu$m.

The original plate for plate making is produced generally by dissolving or dispersing the polymethine compound, image forming component, binder resin and other necessary components in an organic solvent and applying the solution or dispersion to the substrate.

As the solvent used for said application, there may be mentioned water, alcohols such as methyl alcohol, isopropyl alcohol, isobutyl alcohol, cyclopentanol, cyclohexanol and diacetone alcohol, cellosolves such as methylcellosolve and ethylcellosolve, aromatics such as toluene, xylene and chlorobenzene, esters such as ethyl acetate, butyl acetate, isoamyl acetate and methyl propionate, ketones such as acetone, methyl ethyl ketone, methyl isobutyl ketone and cyclohexanone, chlorinated hydrocarbons such as methylene chloride, chloroform and trichloroethylene, ethers such as tetrahydrofuran and dioxane, and aprotic polar solvents such as N,N-dimethylformamide and N-methylpyrrolidone.

Between the substrate and light-to-heat conversion layer, there may be provided a primer layer for the purpose of improving adhesiveness or printability, or the substrate itself may be subjected to surface treatment. Thus, for example, a layer of any of various photosensitive polymres may be cured by exposure to light prior to providing the light-to-heat conversion layer, as disclosed in JP Kokai S60-22903, a layer of an epoxy resin may be heat-cured, as disclosed in JP Kokai S62-50760, a gelatin layer may be hardened, as disclosed in JP Kokai S63-133151 and, further, a urethane resin and a silane coupling agent may be used, as disclosed in JP Kokai H03-200965, or a urethane resin may be used, as disclosed in JP Kokai H03-273248.

As regards the protective layer for surface protection of the light-to-heat conversion layer or silicone rubber layer, transparent films made of polyethylene, polypropylene, polyvinyl chloride, polyvinylidene chloride, polyvinyl alcohol, polyethylene terephthalate or cellophane, for instance, may be used for lamination. Such films may be stretched or oriented prior to application.

EXAMPLES

The following examples illustrate the present invention more specifically. These examples, however, are by no means limitative of the scope of the present invention.

Example 1
Polymethine Compound (Synthesis of Compound (1))

A compound of general formula (II) ($R_1=R_3=R_4$ =methyl, $R_2$=H, D=E=O, $Z_1$=I-) (3.45 g), 0.83 g of a compound of general formula (III) (X=Cl, L=propylene) and 3.36 g of potassium acetate were added to 50 ml of acetic anhydride, and the mixture was stirred at 45–50° C. for 30 minutes and then discharged into 300 ml of a 2% aqueous solution of KI. The resulting crystalline precipitate was collected by filtration, washed with water and recrystallized from isopropanol to give 2.63 g of the compound (1) specifically shown hereinabove.

The elemental analysis data, melting point, absorption maximum wavelength (λmax) and gram extinction coefficient (εg) for or of this compound were as follows:

Elemental analysis ($C_{34}H_{36}ClIN_2O_4$): MW=699.0

|  | C | H | N |
|---|---|---|---|
| Calcd. (%) | 58.42 | 5.19 | 4.01; |
| Found (%) | 58.36 | 5.26 | 3.96. |

Melting point (° C.): 255° C. (decomp.)
λmax: 830 nm (diacetone alcohol solution)
εg: $3.12 \times 10^5$ ml/g·cm The FT-IR spectrum of the compound obtained is shown in FIG. 1.

Figure 7:
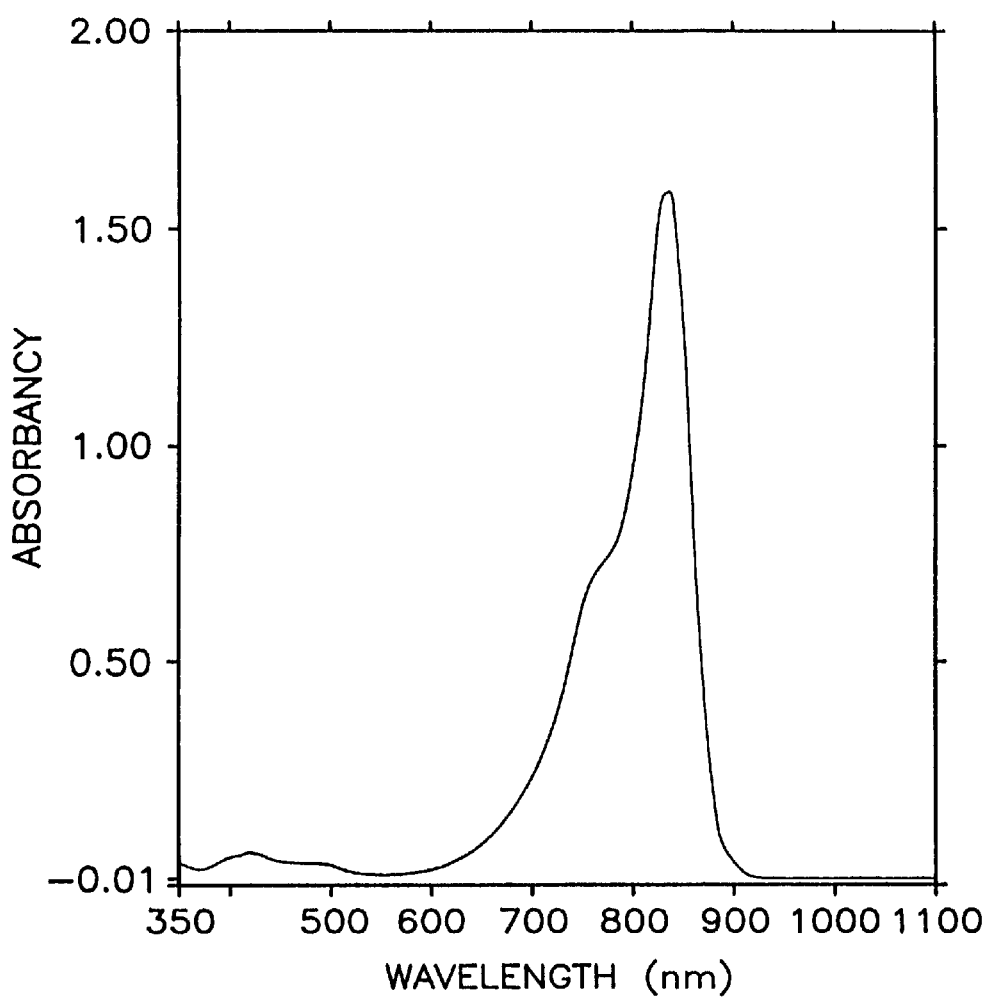
FIG. 7 is a VIS-NIR absorption spectrum of the polymethine compound obtained in Example 1.

The VIS-NIR absorption spectrum of the compound obtained is shown in FIG. 7.

Example 2
Polymethine Compound (Synthesis of Compound (2))

The compound (2) specifically shown hereinabove was obtained in the same manner as in Example 1 except that 3.18 g of the corresponding compound (II) ($R_1=R_3=R_4$= methyl, $R_2$=H, D=E=O, $Z_1=ClO_4^-$) was used and that 300 ml of a 2% aqueous solution of $KClO_4$ was used in lieu of 300 ml of the 2% aqueous solution of KI. The yield was 2.56 g.

The elemental analysis data, melting point, absorption maximum wavelength (λmax) and gram extinction coefficient (εg) for or of this compound were as follows:

Elemental analysis ($C_{34}H_{36}Cl_2N_2O_8$): MW=671.6

|  | C | H | N |
|---|---|---|---|
| Calcd. (%) | 60.81 | 5.40 | 4.17; |
| Found (%) | 60.56 | 5.43 | 4.22. |

Figure 2:
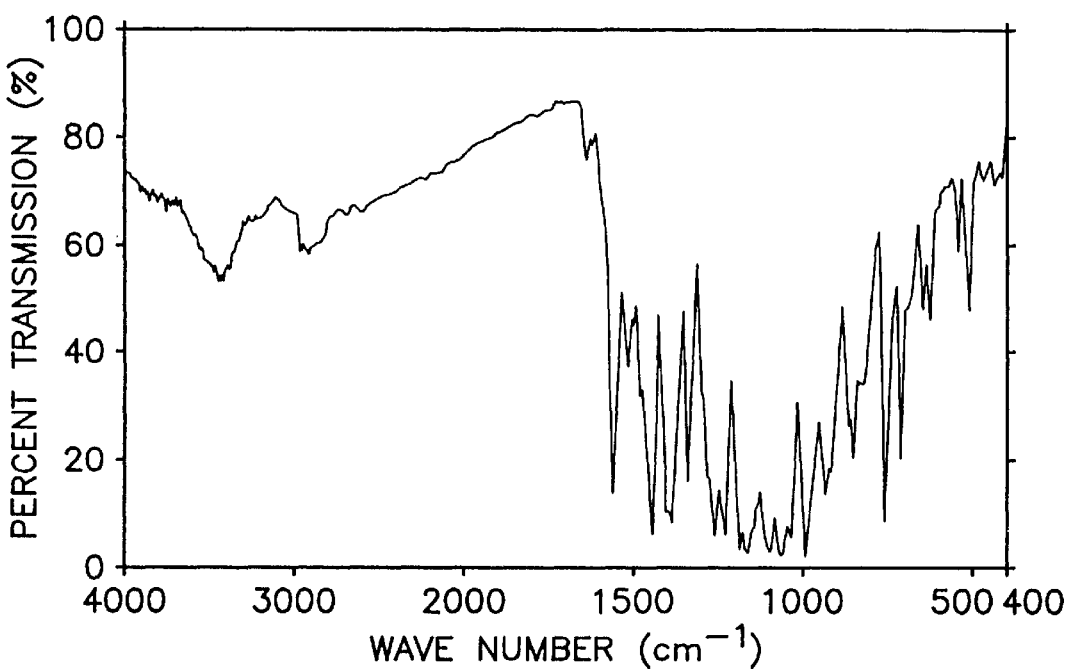
FIG. 2 is an FT-IR spectrum of the polymethine compound obtained in Example 2.

Melting point (° C.): 236° C. (decomp.)
λmax: 830 nm (diacetone alcohol solution)
εg: $3.25 \times 10^5$ ml/g·cm The FT-IR spectrum of the compound obtained is shown in FIG. 2.

Example 3
Polymethine Compound (Synthesis of Compound (3))

The compound (3) specifically shown hereinabove was obtained in the same manner as in Example 1 except that 3.05 g of the corresponding compound (II) ($R_1=R_3=R_4$= methyl, $R_2$=H, D=E=O, $Z_1=BF_4^-$) was used and that 300 ml of a 2% aqueous solution of $KBF_4$ was used in lieu of 300 ml of the 2% aqueous solution of KI. The yield was 2.41 g.

The elemental analysis data, melting point, absorption maximum wavelength (λmax) and gram extinction coefficient (εg) for or of this compound were as follows:

Elemental analysis ($C_{34}H_{36}BClF_4N_2O_4$): MW=658.9

|  | C | H | N |
|---|---|---|---|
| Calcd. (%) | 61.97 | 5.51 | 4.25; |
| Found (%) | 61.89 | 5.55 | 4.19. |

Figure 3:
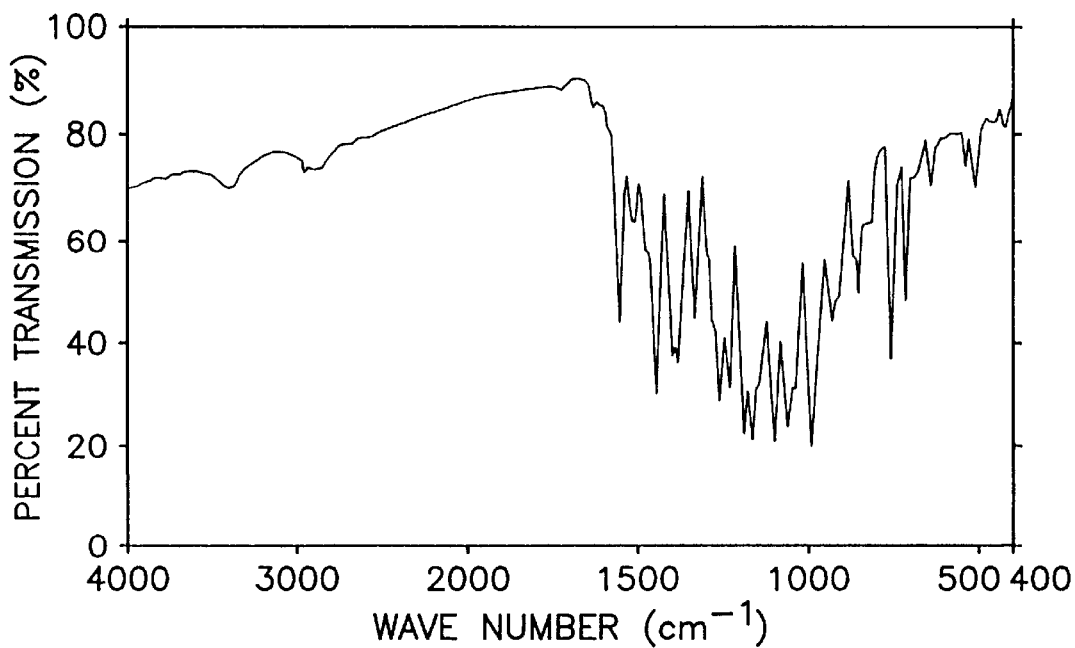
FIG. 3 is an FT-IR spectrum of the polymethine compound obtained in Example 3.

Melting point (° C.) 259° C. (decomp.)
max: 830 nm (diacetone alcohol solution)
εg: $3.20 \times 10^5$ ml/g·cm The FT-IR spectrum of the compound obtained is shown in FIG. 3.

Example 4
Polymethine Compound (Synthesis of Compound (10))

The compound (10) specifically shown hereinabove was obtained in the same manner as in Example 1 except that 3.62 g of the corresponding compound (II) ($R_1$= methoxyethyl, $R_3=R_4$=methyl, $R_2$=H, D=E=O, $Z_1=ClO_4^-$) was used and that 300 ml of a 2% aqueous solution of $KClO_4$ was used in lieu of 300 ml of the 2% aqueous solution of KI. The yield was 2.72 g.

The elemental analysis data, melting point, absorption maximum wavelength ($\epsilon$max) and gram extinction coefficient ($\epsilon$g) for or of this compound were as follows:

Elemental analysis ($C_{38}H_{44}Cl_2N_2O_{10}$): MW=759.7

|  | C | H | N |
|---|---|---|---|
| Calcd. (%) | 60.08 | 5.84 | 3.69; |
| Found (%) | 59.76 | 5.99 | 3.84. |

Figure 4:
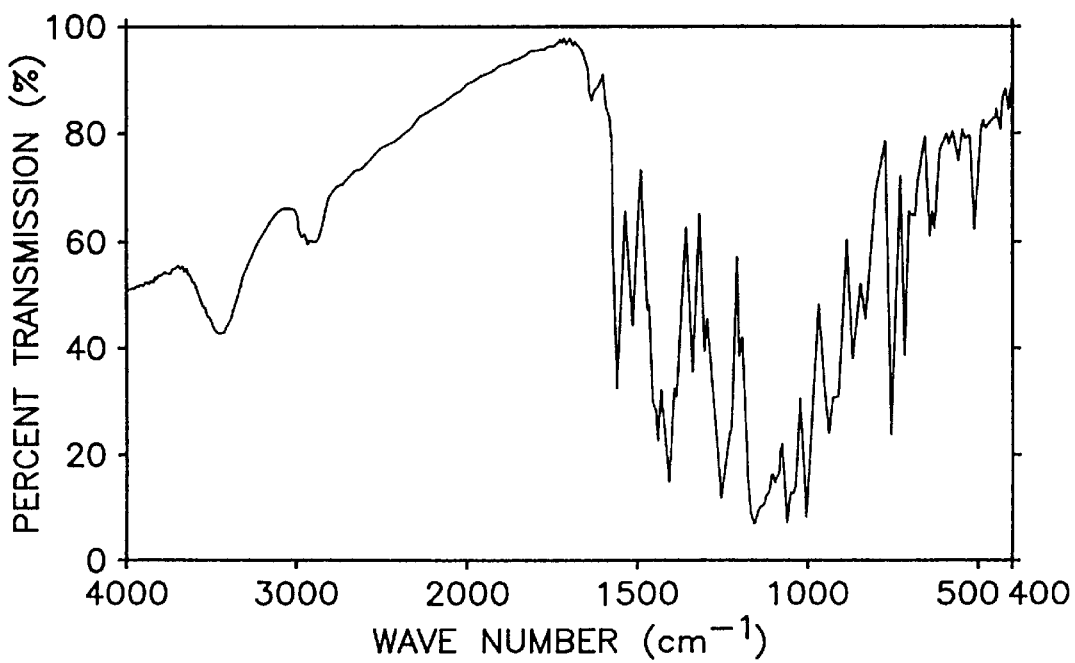
FIG. 4 is an FT-IR spectrum of the polymethine compound obtained in Example 4.

Melting point (° C.): 221° C. (decomp.)
λmax: 834 nm (diacetone alcohol solution)
$\epsilon$g: 2.70×10$^5$ ml/g·cm The FT-IR spectrum of the compound obtained is shown in FIG. 4.

Figure 8:
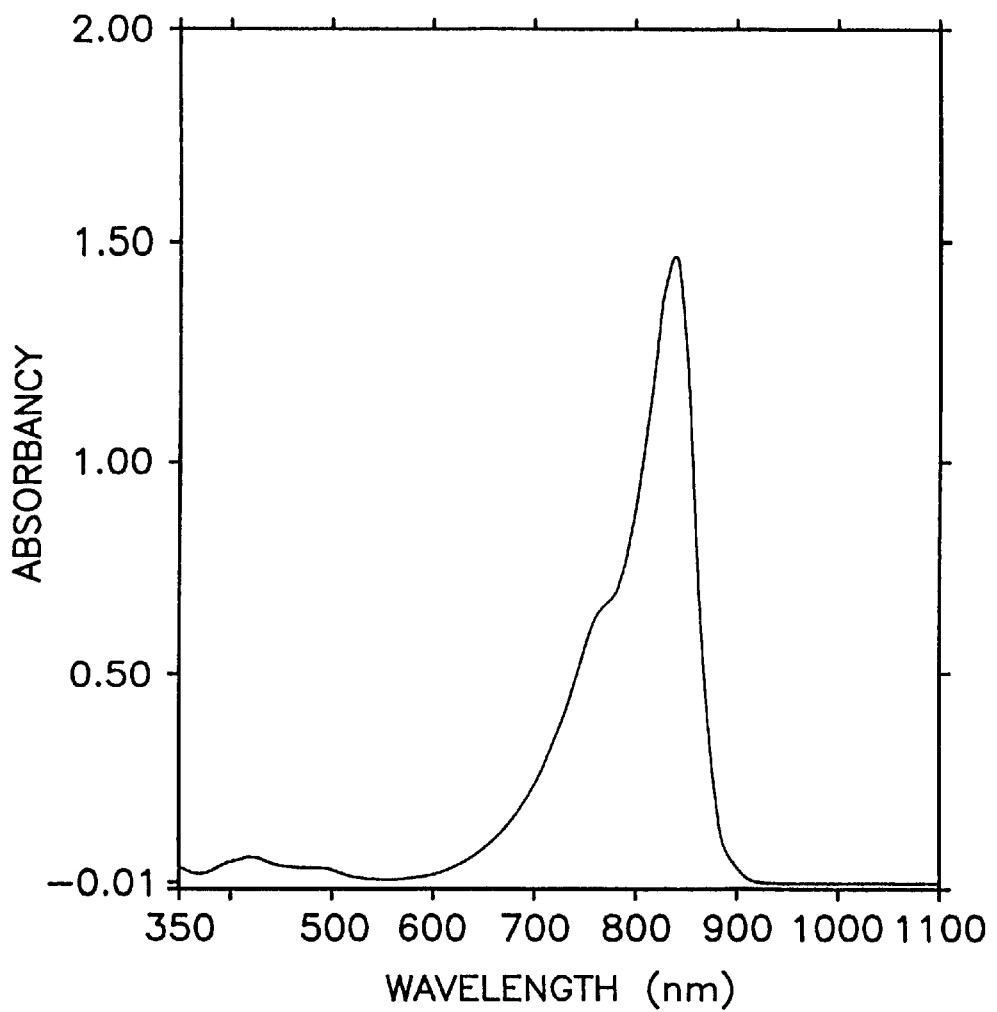
FIG. 8 is a VIS-NIR absorption spectrum of the polymethine compound obtained in Example 4.

The VIS-NIR absorption spectrum of the compound obtained is shown in FIG. 8.

Example 5
Polymethine Compound (Synthesis of Compound (50))

A compound of general formula (II) ($R_1$=3-sulfopropyl, $R_3$=$R_4$=methyl, $R_2$=H, D=E=O, $Z_1$=nil) (3.25 g), 1.80 g of a dianil compound of general formula (IV) (X=Cl, L=propylene) and 3.36 g of potassium acetate were added to 50 ml of acetic anhydride, and the mixture was stirred at 65–70° C. for 60 minutes, 200 ml of isopropanol was then added, and the resulting mixture was further stirred at the same temperature for 60 minutes. After evaporation to dryness, 100 ml of ethyl acetate was added, and the mixture was stirred at room temperature for an hour. The resulting crystalline precipitate was collected by filtration, washed with 10 ml of ethyl acetate and recrystallized from 100 ml of methanol. The crystals obtained were dissolved in a solution composed of 2 g of sodium acetate, 100 ml of methanol and 100 ml of isopropanol, and the solvents were distilled off at ordinary pressure. The resulting crystalline precipitate was collected by filtration and dried to give 1.24 g of the compound (50) specifically shown hereinabove.

The elemental analysis data, melting point, absorption maximum wavelength (λmax) and gram extinction coefficient ($\epsilon$g) for or of this compound were as follows:

Elemental analysis ($C_{38}H_{42}ClN_2NaO_{10}S_2$): MW=809.3

|  | C | H | N |
|---|---|---|---|
| Calcd. (%) | 56.39 | 5.23 | 3.46; |
| Found (%) | 56.17 | 5.40 | 3.40. |

Figure 5:
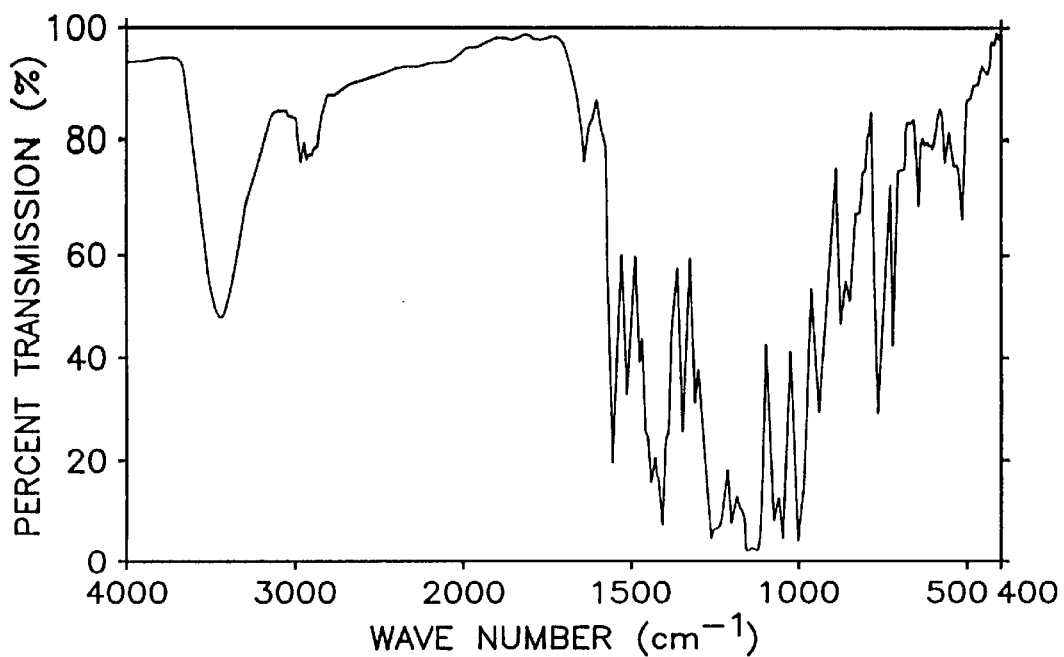
FIG. 5 is an FT-IR spectrum of the polymethine compound obtained in Example 5.

Melting point (° C.): >260° C.
λmax: 827 nm (methanol solution)
$\epsilon$g: 2.45×10$^5$ ml/g·cm The FT-IR spectrum of the compound obtained is shown in FIG. 5.

Figure 9:
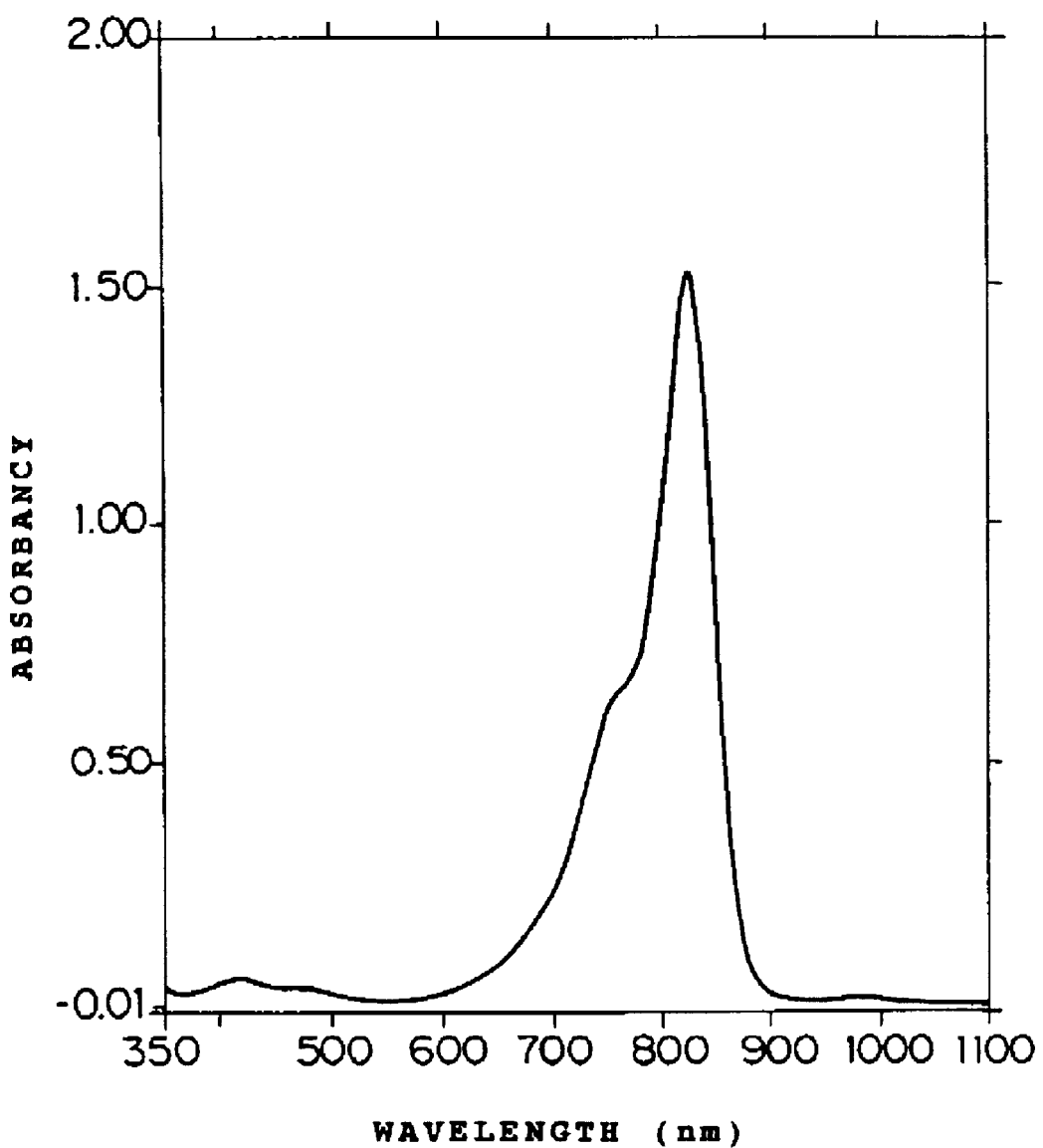
FIG. 9 is a VIS-NIR absorption spectrum of the polymethine compound obtained in Example 5.

The VIS-NIR absorption spectrum of the compound obtained is shown in FIG. 9.

Example 6
Polymethine Compound (Synthesis of Compound (55))

A compound of general formula (II) ($R_1$=$R_3$=$R_4$=methyl, $R_2$=H, D=E=O, $Z_1$=ClO$_4^-$) (3.18 g), 1.73 g of a compound of general formula (IV) (X=Cl, L=ethylene) and 3.36 g of potassium acetate were added to 50 ml of acetic anhydride, and the mixture was stirred at 45–50° C. for 30 minutes and then discharged into 300 ml of a 2% aqueous solution of KClO$_4$. The resulting crystalline precipitate was collected by filtration, washed with water and recrystallized from isopropanol to give 2.00 g of the compound (55) specifically shown hereinabove.

The elemental analysis data, melting point, absorption maximum wavelength (λmax) and gram extinction coefficient ($\epsilon$g) for or of this compound were as follows:

Elemental analysis ($C_{33}H_{34}Cl_2N_2O_8$): MW=657.5

|  | C | H | N |
|---|---|---|---|
| Calcd. (%) | 60.28 | 5.21 | 4.26; |
| Found (%) | 60.20 | 5.24 | 4.22. |

Figure 6:
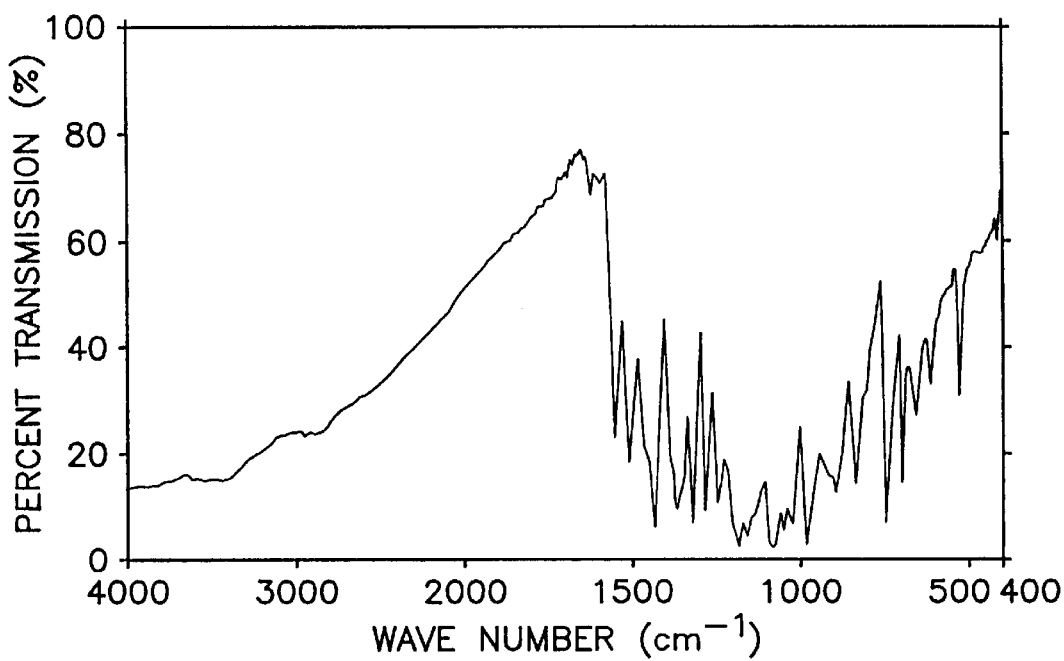
FIG. 6 is an FT-IR spectrum of the polymethine compound obtained in Example 6.

Melting point (° C.): 225° C. (decomp.)
λmax: 857 nm (diacetone alcohol solution)
$\epsilon$g: 3.35×10$^5$ ml/g·cm The FT-IR spectrum of the compound obtained is shown in FIG. 6.

Figure 10:
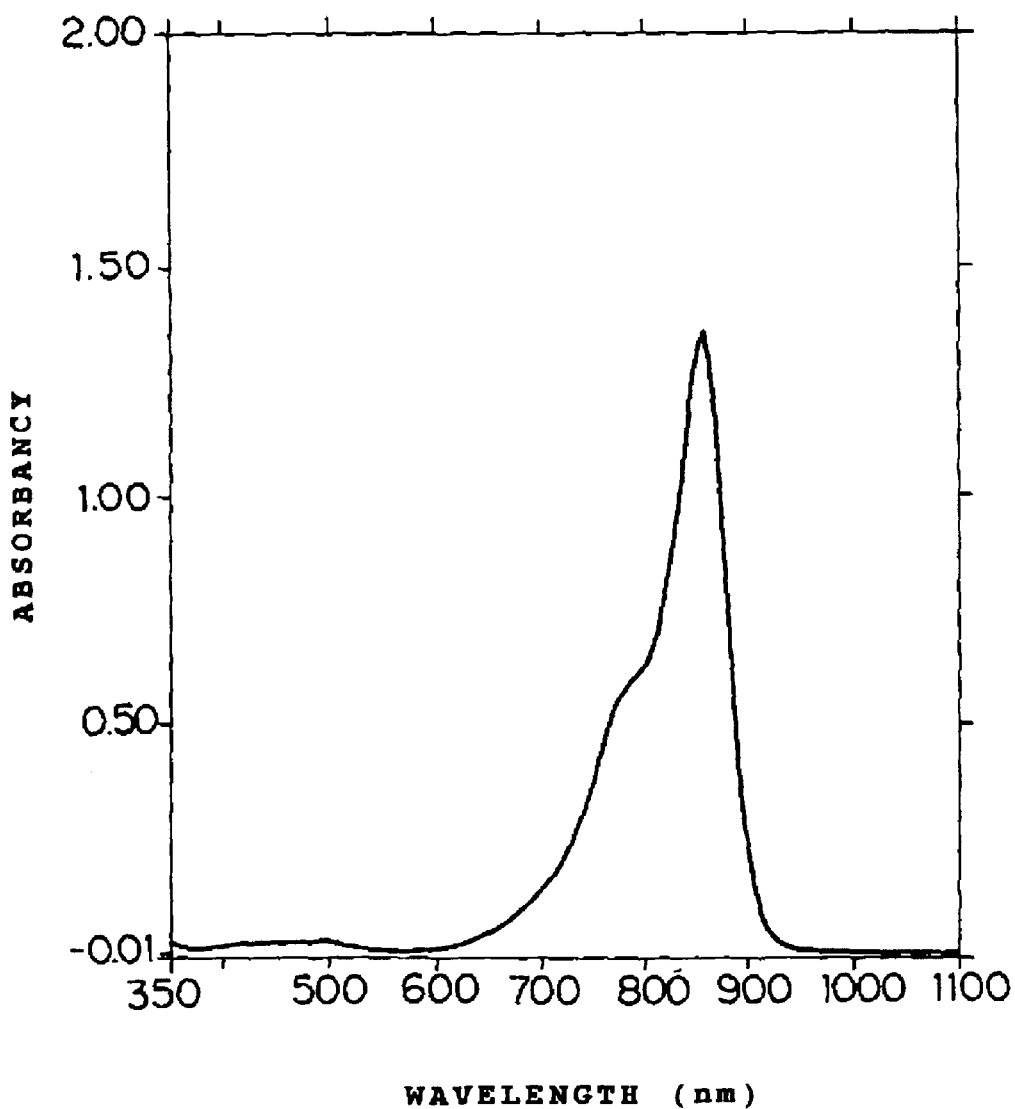
FIG. 10 is a VIS-NIR absorption spectrum of the polymethine compound obtained in Example 6.

The VIS-NIR absorption spectrum of the compound obtained is shown in FIG. 10.

Example 7
Polymethine Compound (Synthesis of Compound (72))

The compound (72) specifically shown hereinabove was obtained in the same manner as in Example 6 except that 3.62 g of the corresponding compound (II) ($R_1$=methoxyethyl, $R_3$=$R_4$=methyl, $R_2$=H, D=E=O, $Z_1$=ClO$_4^-$) was used. The yield was 2.20 g.

The elemental analysis data, melting point, absorption maximum wavelength (λmax) and gram extinction coefficient ($\epsilon$g) for or of this compound were as follows:

Elemental analysis ($C_{37}H_{42}Cl_2N_2O_{10}$): MW=745.6

|  | C | H | N |
|---|---|---|---|
| Calcd. (%) | 59.60 | 5.68 | 3.76; |
| Found (%) | 59.51 | 5.61 | 3.70. |

Melting point (° C.) 217° C. (decomp.)
λmax: 862 nm (diacetone alcohol solution)
$\epsilon$g: 3.20×10$^5$ ml/g·cm Example 8
Polymethine Compound (Synthesis of Compound (96))

The compound (96) specifically shown hereinabove was obtained in the same manner as in Example 5 except that 3.21 g of the corresponding compound (II) ($R_1$=3-sulfopropyl, $R_3$=$R_4$=methyl, $R_2$=H, D=E=methylene, $Z_1$=nil) and 1.73 g of a dianil compound of general formula (IV) (X=Cl, L=ethylene) were used. The yield was 1.30 g.

The elemental analysis data, melting point, absorption maximum wavelength (λmax) and gram extinction coefficient ($\epsilon$g) for or of this compound were as follows:

Elemental analysis ($C_{42}H_{50}ClN_2NaO_6S_2$): MW=787.4

|  | C | H | N |
|---|---|---|---|
| Calcd. (%) | 62.54 | 6.14 | 3.56; |
| Found (%) | 62.39 | 6.27 | 3.51. |

Melting point (° C.): >260° C.
λmax: 833 nm (methanol solution)
$\epsilon$g: 2.50×10$^5$ ml/g·cm

Example 9
Production of a Near Infrared Absorber-containing Material

A sample was produced by applying, to a polyethylene terephthalate (PET) film having an average thickness of 5 µm, a solution of 10 g of Delpet 80N (acrylic resin; product of Asahi Chemical Industry; as a binder) and 0.2 g of the above compound (1) in 90 g of a toluene-methyl ethyl ketone (1/1) mixture using a wire bar to give a dry film thickness of about 5 µm.

Laser beams from a single mode semiconductor laser (wavelength: 830 nm) were converged by means of a lens so that a beam diameter of 10 µm might be attained on the surface of said sample. The semiconductor was adjusted so that the power of the laser beam arriving at said surface might be varied within the range of 50 to 200 mW. The sample was thus irradiated with a single pulse at a pulse width of 20 µs. After completion of the irradiation, the sample was observed under the light microscope. When the laser power arriving at the surface was 50 mW, through hole formation with a diameter of about 10 µm was confirmed.

Example 10
Production of a Near Infrared Absorber-containing Material

The procedure of Example 9 was followed in the same manner except that 0.2 g of the compound (10) was used in lieu of 0.2 g of the compound (1). The sample after completion of the irradiation was examined under an optical microscope, whereupon through hole formation with a diameter of about 10 µm was confirmed when the laser power arriving at the surface was 50 mW.

Example 11
Making of a Plate for Direct Printing Plate Making
(Formation of an Undercoat Layer)

On a polyethylene terephthalate film having a thickness of 175 µm, there was formed a gelatin layer as a primer layer so that the dry film thickness of said gelatin layer amounted to 0.2 µm.

(Formation of a Light-to-Heat Conversion Layer)

A light-to-heat conversion layer was formed by applying a coating composition prepared in accordance with the recipe given below to the above gelatin-coated polyethylene terephthalate film to a dry film thickness of 2 µm.

| | |
|---|---|
| Compound No. (1) | 0.1 weight part |
| Crisvon 3006LV (polyurethane; Product of Dainippon Ink and Chemicals) | 5.0 weight parts |
| Solsperse S27000 (product of ICI) | 0.4 weight part |
| Nitrocellulose (containing 30% of n-propanol) | 4.2 weight parts |
| Xylylenediamine (1 mole)-glycidyl methacrylate (4 moles) adduct | 2.0 weight parts |
| Ethyl Michler's ketone | 0.2 weight part |
| Tetrahydrofuran | 90 weight parts |
| (Formation of a silicone rubber layer) | |

A silicone rubber layer was formed on the above light-to-heat conversion layer by applying thereto a coating composition prepared in accordance with the recipe given below to a dry film thickness of 2 µm.

| | |
|---|---|
| α,ω-Divinylpolydimethylsiloxane (degree of polymerization: ca 700) $(CH_3)_3Si-O-(SiH(CH_3)-O-)_8-Si(CH_3)_3$ | 9.0 weight parts |
| | 0.6 weight part |
| Polydimethylsiloxane (degree of polymerization: ca 8,000) | 0.5 weight part |
| Olefin-chloroplatinic acid | 0.08 weight part |
| Inhibitor $HC\equiv C-C(CH_3)_2-O-Si(CH_3)_3$ | 0.07 weight part |
| Isopar (product of Esso Chemical) | 55 weight parts |

Writing was made on the fresh printing plate obtained in the above manner, using a semiconductor laser with an oscillation wavelength of 830 nm and a beam diameter of 10 µm. The power on the plate was 110 mW. A printing plate with sharp edges could be formed; the laser recording sensitivity was 200 mJ/cm$^2$ and the resolution was 8 µm.

Example 12
Making of a Plate for Direct Printing Plate Making

A plate for direct printing plate making was produced in the same manner as in Example 11 except that 0.1 weight part of the compound (2) was used in lieu of 0.1 weight part of the compound (1).

Writing was made on the fresh printing plate obtained in the above manner, using a semiconductor laser with an oscillation wavelength of 830 nm and a beam diameter of 10 µm. The power on the plate was 110 mW. A printing plate with sharp edges could be formed; the laser recording sensitivity was 200 mJ/cm$^2$ and the resolution was 8 µm.

Example 13
Making of a Plate for Direct Printing Plate Making

A plate for direct printing plate making was produced in the same manner as in Example 11 except that 0.1 weight part of the compound (10) was used in lieu of 0.1 weight part of the compound (1).

Writing was made on the fresh printing plate obtained in the above manner, using a semiconductor laser with an oscillation wavelength of 830 nm and a beam diameter of 10 µm. The power on the plate was 110 mW. A printing plate with sharp edges could be formed; the laser recording sensitivity was 200 mJ/cm$^2$ and the resolution was 8 µm.

Comparative Example 1

The procedure of Example 9 was followed in the same manner except that 0.2 g of the polymethine compound having the structural formula shown below, which is described in JP Kokai S63-319191, was used in lieu of 0.2 g of the compound (1). In a light microscopic examination of the sample after completion of the irradiation, no through hole formation was observed even when the laser power arriving at the surface was 100 mW.

Compound A

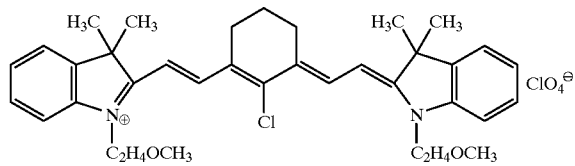

Comparative Example 2

The procedure of Example 9 was followed in the same manner except that 0.2 g of the polymethine compound having the structural formula shown below, which is described in JP Kokai H02-229865, was used in lieu of 0.2 g of the compound (1). In a light microscopic examination of the sample after completion of the irradiation, no through hole formation was observed even when the laser power arriving at the surface was 100 mW.

an alkoxyalkyl group containing, as a whole, 2 to 8 carbon atoms, a sulfoalkyl group containing 1 to 8 carbon atoms or a carboxyalkyl group containing, as a whole, 2 to 9 carbon atoms.

Compound B

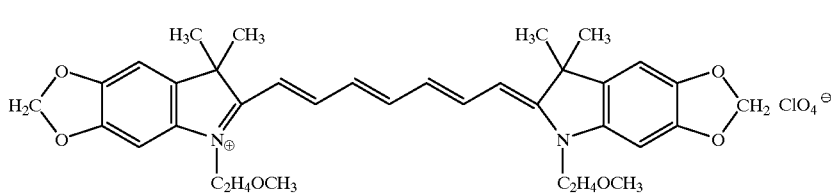

EFFECTS OF THE INVENTION

The polymethine compound of general formula (I) shows less absorption in the visible region, and the near infrared absorber comprising this compound can be used with advantage in laser thermal transfer recording materials and laser heat-sensitive recording materials having good sensitivity to laser light with a high light-to-heat conversion efficiency and, therefore, enabling high-speed recording. The polymethine compound of general formula (I) is very highly soluble in various solvents used for making the light-to-heat conversion layer of starting plates for direct printing plate making and has good compatibility with various binder resins and other components, facilitating preparation of coating compositions. It can thus form uniform light-to-heat conversion layers and is particularly suited for use in the manufacture of starting plates for direct printing plate making.

What is claimed is:

1. A polymethine compound which has the following general formula:

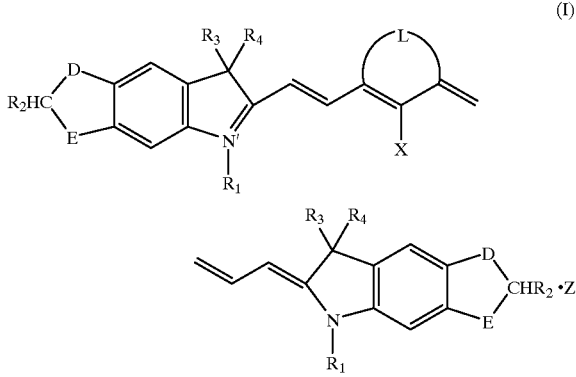

wherein $R_1$ represents an alkyl group, which may optionally be substituted, $R_2$ represents a hydrogen atom or a lower alkyl group, $R_3$ and $R_4$ each independently represents a lower alkyl group or $R_3$ and $R_4$ may combinedly form a cyclic structure, L is an alkylene group which is required for the formation of a cyclic structure and may optionally be substituted, one or more carbon atoms of which cyclic structure may be replaced by some other atom(s) or atomic group(s), D and E each independently represents an oxygen atom or a methylene group, X represents a hydrogen or halogen atom or a substituted amino group, and Z represents a charge-neutralizing ion.

2. A polymethine compound as claimed in claim 1, wherein $R_1$ is an alkyl group containing 1 to 8 carbon atoms, 3. A polymethine compound as claimed in claim 1 wherein L is an alkylene group containing 2 to 4 carbon atoms.

4. A polymethine compound as claimed in claim 1, wherein Z is $Cl^-$, $Br^-$, $I^-$, $ClO_4^-$, $BF_4^-$, $CF_3CO_2^-$, $PF_6^-$, $SbF_6^-$, $CH_3SO_3^-$, a p-toluenesulfonate ion, $Na^+$, $K^+$ or a triethylammonium ion.

5. A polymethine compound as claimed in claim 1 wherein each of $R_3$ and $R_4$ is a methyl group or $R_3$ and $R_4$ combinedly form a cyclopentane or cyclohexane group together with the carbon atom to which they are bound.

6. A polymethine compound as claimed in claim 1 wherein X is H, Cl, Br or a diphenylamino group.

7. A method of producing the polymethine compound of claim 1 which comprises subjecting an indolenium compound represented by the general formula (II):

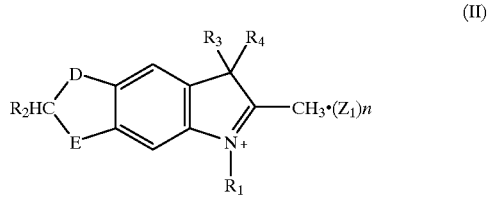

wherein $R_1$ represents an alkyl group, which may optionally be substituted, $R_2$ represents a hydrogen atom or a lower alkyl group, $R_3$ and $R_4$ each independently represents a lower alkyl group or $R_3$ and $R_4$ may combinedly form a cyclic structure, D and E each independently represents an oxygen atom or a methylene group, $Z_1$ represents a charge-neutralizing ion and n represents an integer of 0 or 1, and a diformyl compound represented by the general formula (III):

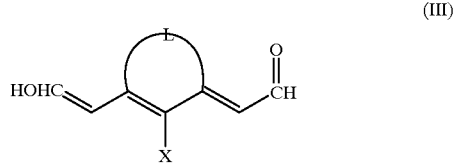

wherein X represents a hydrogen or halogen atom or a substituted amino group and L is an alkylene group which is required for the formation of a cyclic structure and may optionally be substituted, one or more carbon atoms of which cyclic structure may be replaced by some other atom(s) or atomic group(s), or a dianil compound represented by the general formula (IV):

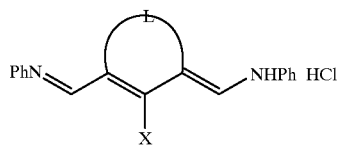

(IV)

wherein X represents a hydrogen or halogen atom or a substituted amino group and L is an alkylene group which is required for the formation of a cyclic structure and may optionally be substituted, one or more carbon atoms of which cyclic structure may be replaced by some other atom(s) or atomic group(s), to condensation reaction in the presence of a fatty acid salt and a dehydrating organic acid.

8. A near infrared absorber which comprises the polymethine compound of claim 1.

9. An original plate for direct plating for printing comprising a light-to-heat conversion layer formed on a substrate, characterized in that said light-to-heat conversion layer contains the polymethine compound of claim 1.

10. A method of making a printing plate which comprises irradiating the original plate for direct plating of claim 9 with a laser beam from a light source laser which has a light emission wavelength region within the range of 750 nm to 900 nm.

* * * * *